(12) United States Patent
Matsumoto et al.

(10) Patent No.: US 8,722,126 B2
(45) Date of Patent: *May 13, 2014

(54) COMPOSITIONS FOR FOOD, PROCESS FOR PRODUCING THE SAME, AND FUNCTIONAL FOODS AND DRINKS CONTAINING THE SAME

(75) Inventors: Hitoshi Matsumoto, Saitama (JP); Shigeru Tominaga, Saitama (JP); Mitsuo Kishi, Saitama (JP); Takashi Kawakami, Saitama (JP); Takahisa Tokunaga, Saitama (JP); Masao Hirayama, Saitama (JP)

(73) Assignee: Meiji Co., Ltd., Tokyo (JP)

( * ) Notice: Subject to any disclaimer, the term of this patent is extended or adjusted under 35 U.S.C. 154(b) by 1242 days.

This patent is subject to a terminal disclaimer.

(21) Appl. No.: 12/585,783

(22) Filed: Sep. 24, 2009

(65) Prior Publication Data
US 2010/0015065 A1   Jan. 21, 2010

Related U.S. Application Data

(63) Continuation of application No. 10/019,402, filed as application No. PCT/JP00/04337 on Jun. 30, 2000, now Pat. No. 7,658,963.

(30) Foreign Application Priority Data

Jul. 2, 1999  (JP) .................................. 1999-188998
Nov. 12, 1999 (JP) .................................. 1999-321978

(51) Int. Cl.
| A23L 2/06  | (2006.01) |
| A23L 1/29  | (2006.01) |
| B01D 61/02 | (2006.01) |
| A61K 36/45 | (2006.01) |
| A61K 36/00 | (2006.01) |
| A23G 3/36  | (2006.01) |
| A23G 1/42  | (2006.01) |
| A23G 4/12  | (2006.01) |

(52) U.S. Cl.
CPC ............... *A23G 3/368* (2013.01); *A23G 1/426* (2013.01); *A23G 4/126* (2013.01)
USPC ............ 426/489; 426/590; 426/599; 424/732

(58) Field of Classification Search
USPC .......... 426/478, 489, 590, 599; 424/123, 124, 424/725, 732, 777; 210/634, 652
See application file for complete search history.

(56) References Cited

U.S. PATENT DOCUMENTS

| 4,083,779 A | 4/1978 | Combe et al. |
| 4,211,577 A | 7/1980 | Wallin |
| 4,643,902 A | 2/1987 | Lawhon et al. |
| 5,196,449 A | 3/1993 | Magistretti et al. |
| 5,200,186 A | 4/1993 | Gabetta et al. |
| 6,780,442 B2 | 8/2004 | Bailey et al. |
| 7,658,963 B1 * | 2/2010 | Matsumoto et al. .......... 426/590 |
| 2002/0055471 A1 | 5/2002 | Bailey et al. |

FOREIGN PATENT DOCUMENTS

| EP | 1208755 A1 * | 5/2002 | ................ A23L 1/30 |
| GB | 1007751 | 10/1965 | |
| GB | 1235379 | 6/1971 | |
| JP | B2-58-50633 | 11/1983 | |
| JP | B32-59-223756 | 12/1984 | |
| JP | B2-60-31225 | 7/1985 | |
| JP | A-03-81220 | 4/1991 | |
| JP | A-03-99090 | 4/1991 | |
| JP | A-09-84564 | 3/1997 | |
| WO | WO 01/01798 | 1/2001 | |

OTHER PUBLICATIONS

PCT International Search Report mailed on Oct. 3, 2000 for the corresponding International patent application No. PCT/JP2000/04337.

European Search Report dated Jul. 18, 2002 in corresponding European patent application No. EP 00 94 2413.

Osami Kajimoto, et al., "A function and effect of blueberry clinical study of the effect of blueberry extract on asthenopia and mental strain," Shokuhin kogyo (The Food Industry), (Aug. 30, 1998), pp. 29-35 (Partial English translation provided).

(Continued)

*Primary Examiner* — My-Chau T Tran
(74) *Attorney, Agent, or Firm* — Posz Law Group, PLC

(57) ABSTRACT

Black currant anthocyanin-containing compositions for foods comprising 1 to 25% by weight of black currant anthocyanin on the basis of solid matters; a process for producing a black currant anthocyanin-containing composition for foods characterized by purifying and concentrating black currant juice employed as a starting material by using a charged reverse osmosis membrane; functional foods and drinks characterized by containing the above compositions for foods; and the above-described compositions for foods and the above-described functional foods and drinks having an effect of improving visual function, a function of improving blood fluidity, and/or a function of lowering blood pressure. The conventional black currant anthocyanin compositions have a low black currant anthocyanin content, strong acidity and poor stability, which makes them unsuitable as additives for foods and drinks. However, the production process according to the present invention makes it possible to provide black currant anthocyanin-containing compositions for foods which have a high black currant anthocyanin content, an adequate acidity, and a high stability and can be added to foods and drinks. Moreover, functional foods and drinks containing these compositions, which have an effect of improving visual function, a function of improving blood fluidity, or a function of lowering blood pressure, can be provided.

21 Claims, 2 Drawing Sheets

(56) References Cited

OTHER PUBLICATIONS

Saburo Itoh, "A function and effect of blueberry recent matters and future perspectives of blueberry," Shokuhin kogyo (The Food Industry), (Aug. 30, 1998), pp. 16-21 (English abstract provided).

G. Baumann, "New ways of coloured juice treatment," Confructa studien, pp. 137-140, 142-148, and 150-151, (1989).

Toujirou Tsushida, "Remarkable healthy materials and the functional study of the same physiological functionality of blueberry," Shokuhin to kaihatsu (up-to-date food processing), vol. 31, No. 3, pp. 5-8 (Partial English translation provided).

Hideo Nakamura, "Functionality of blueberry and the use and processing of blueberry development and use of blueberry extract," Shokuhin kogyo (The Food Industry), (Aug. 30, 1997), pp. 47-55 (Partial English translation provided).

Isao Tomita, et al., "Functionality of blueberry and the use and processing of blueberry antioxidant function of blueberry," Shokuhin kogyo (The Food Industry), (Aug. 30, 1997), pp. 40-45 (Partial English translation provided).

Tojiro Tsushida, "Functionality of blueberry and the use and processing of blueberry physiological functionality of blueberry," Shokuhin kogyo (The Food Industry), (Aug. 30, 1997), pp. 34-39 (Partial English translation provided).

Saburo Itoh, "Functionality of blueberry and the use and processing of blueberry splendid functionality and health," Shokuhin kogyo (The Food Industry); (Aug. 30, 1997), pp. 16-23 (Partial English translation provided).

J. Banaszczyk, et al., "Suitability of Blackcurrants for Juices and Clear Nectars Production," *Fruit Processing*, (Aug. 1996), pp. 321-325.

C.D. Chiriboga, et al., Ion Exchange Purified Anthocyanin Pigments as a Colorant for Cranberry Juice Cocktail, *Journal of Food Science*, (1973), Department of Food Science and Technology, University of Massachusetts, vol. 38, pp. 464-467.

Cristina T. da Costa, et al., "Separation of blackcurrant anthocyanins by capillary zone electrophoresis," *Journal of Chromatography*, (1998), No. 799, pp. 321-327.

Hitoshi Nakaishi, et al., "Effect of Black Currant Anthocyanoside Intake on Dark Adaptation and VDT Work-induced Transient Refractive Alteration in Healthy Humans," *Alternative Medicine Review*, (2000), vol. 5, No. 6, pp. 553-562.

Hitoshi Matsumoto, et al., "Preparative-Scale Isolation of Four Anthocyanin Components of Black Currant (*Ribes nigrum* L.) Fruits," *Journal of Agricultural and Food Chemistry*, (2001), vol. 49, pp. 1541-1545.

Cato Frøytlog, et al., "Combination of chromatographic techniques for the preparative isolation of anthocyanins—applied on blackcurrant (*Ribes nigrum*) fruits," *Journal of Chromatography A*, (1998), vol. 825, pp. 89-95.

Uno Viberg, et al., "A study of some important vitamins and antioxidants in a blackcurrant jam with low sugar contents and without additives," *International Journal of Food Sciences and Nutrition*, (1997), vol. 48, pp. 57-66.

Yasuhiko Maeda, "Quality rating of the foods containing anthocyan pigment," Shokuhin Kaihatsu, (1984) vol. 19, No. 6, pp. 27-30 (Partial English translation provided).

Saburo Ito, "Development of Berry Species Kind," Shokuhin Kaihatsu, (1984), vol. 19, No. 6, pp. 12-18 (Partial English translation provided).

M. Sato, et al., "Composition of blueberry anthocyanins and the physiological effects of ingestion of blueberry wine," Wines and Spirits Research Center, Mercian Corp., Japan (English abstract provided).

Lakshminarayan P. Raman et al., "Consider Nanofiltration for Membrane Separations," *Chemical Engineering Progress*, (Mar. 1994), pp. 68-70.

Dr. Paolo Morazzoni, "A function and effect of blueberry chemical properties, pharmacology, clinical matters of standardized myltille dried extract," Shokuhin kogyo (The Food Industry), (Aug. 30, 1998), pp. 36-45 (Partial English translation provided).

F.G. Nakhmedov et al., "Coloring Agents from the wastes of chokeberry and black currant processing," (1975), Koneservnaya I Ovoshchesushil'naya Promyshlennost, vol. 4, pp. 15, 16, 18 (English translation provided).

Scheme showing the process of purifying a coloring agent proposed in Nakhmedov (one page) (attached to preliminary amendment).

Boccorh et al., "Factors influencing quantities of sugars and organic acids and blackcurrant concentrates," Z Lebensm Unters Forsch A, (1998), No. 206, pp. 273-278 (attached to preliminary amendment).

Sanna Viljakainen, "Reduction of Acidity in Northern Region Berry Juices," ISBN 951-22-6435-8, (2003) (4 pages), (attached to preliminary amendment).

* cited by examiner

|  | R₁ | R₂ |
|---|---|---|
| delphinidin | OH | OH |
| cyanidin | OH | H |
| malvidin | OCH₃ | OCH₃ |
| peonidin | OCH₃ | H |
| petunidine | OH | OCH₃ |

Gly represents saccharide (for example, glucose, galactose, and rutinose).

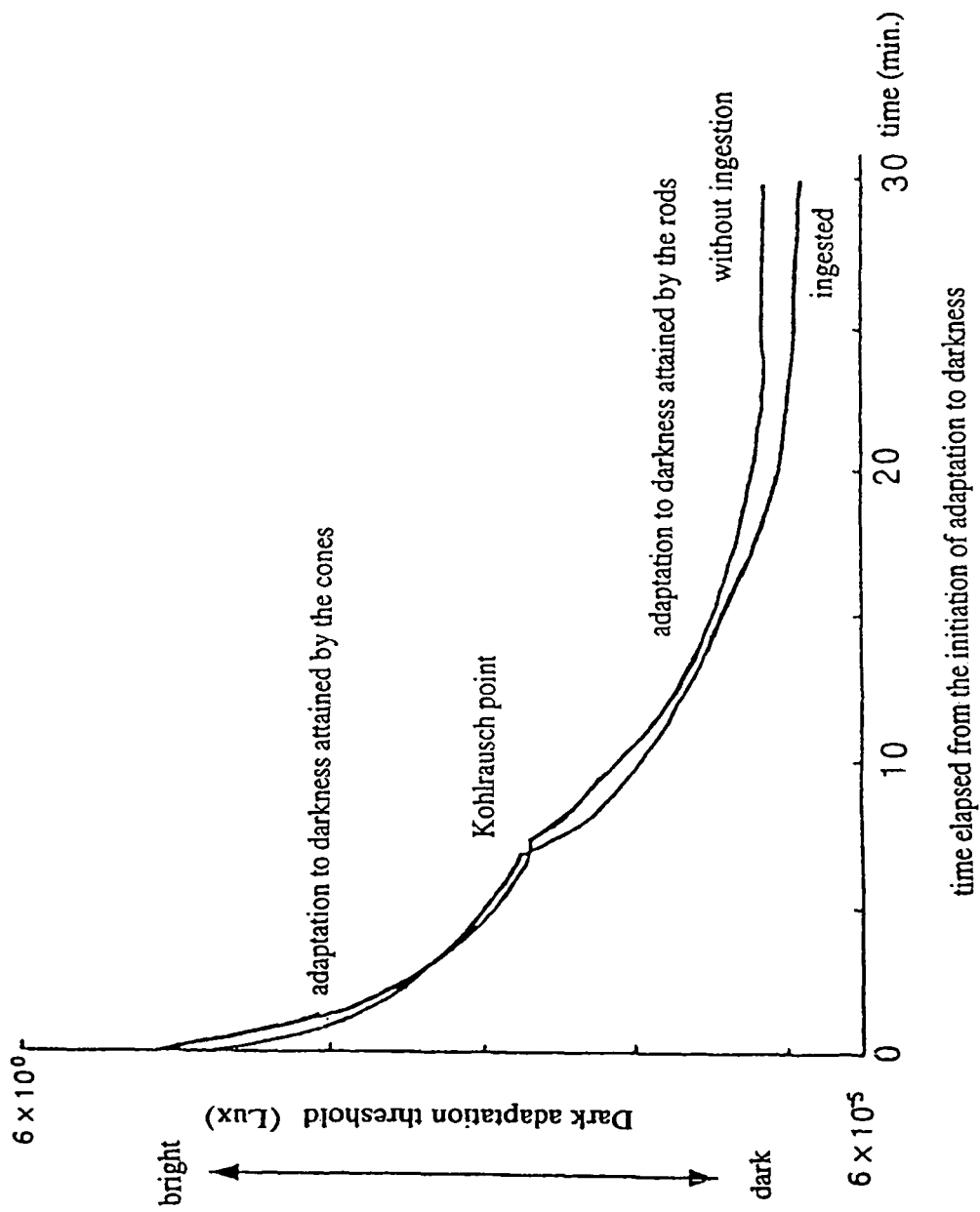

COMPOSITIONS FOR FOOD, PROCESS FOR PRODUCING THE SAME, AND FUNCTIONAL FOODS AND DRINKS CONTAINING THE SAME

CROSS REFERENCE TO RELATED APPLICATIONS

This application is a continuation application of U.S. patent application Ser. No. 10/019,402 filed on Dec. 28, 2001 and entitled COMPOSITIONS FOR FOOD, PROCESS FOR PRODUCING THE SAME, AND FUNCTIONAL FOODS AND DRINKS CONTAINING THE SAME, now U.S. Pat. No. 7,658,963 B1, which in turn is a PCT National Stage of PCT Application No. PCT/JP2000/04337 filed on Jun. 30, 2000, and which claims priority from Japanese Application No. 11-188988 filed on Jul. 2, 1999, and No. 11-321978 filed on Nov. 12, 1999, the contents of each being incorporated herein by reference.

FIELD OF THE INVENTION

The present invention relates to black currant anthocyanin-containing compositions for foods comprising a specific amount of black currant anthocyanin, a process for producing the same, the compositions for foods having a visual function improvement effect, blood fluidity improvement function, or blood pressure lowering function, and functional foods and drinks having these functions which comprise the compositions for foods.

BACKGROUND ART

Black currant (nomenclature: *Ribes. nigrum*) is a plant that belongs to genus *saxifraga* (or genus *hydrangea* depending on classification). Because of the distinctive flavor, taste, acidity and the like of black currant fruit, black currant has been employed as a starting material for jams, fruit juice, alcohol beverages and the like for example in Europe. The black currant is edible in an uncooked state although it is not employed in that manner often due to its strong acidity. Fresh juice just squeezed from black currant has a solids concentration (Bx) of about 10%, and contains about 20 to 30% by weight of organic acids such as citric acid and malic acid on the basis of solid matters, and about 30 to 50% by weight of monosaccharide on the basis of solid matters. This makes acidity and sweetness excessively strong. Therefore, only a small amount thereof could be added to, for example, drinks such as juice, and gelatinous foods. To other foods, it was not added at all.

Fruit juice concentrate is commercially available as a starting material for these drinks. This is provided by squeezing fresh juice from fruit, followed by the removal of only water with the aid of, for example, an uncharged reverse osmosis membrane to prepare an approximately six-fold concentrate. In general, in the case of six-fold concentrates of apple juice, orange juice and the like, dilution with water, the volume of which is six times greater than that of the fruit, produces 100% fruit juice as a reduced product from fruit juice concentrate. However, in the case of black currant juice concentrate, as with the case of the fresh juice, the concentrate comprises about 20 to 30% by weight of organic acids such as citric acid and malic acid on the basis of solid matters, and about 30 to 50% by weight of monosaccharide on the basis of solid matters, and thus, acidity is excessively strong. Therefore, it was impossible to produce 100% fruit juice from black currant.

It is known that black currant contains an anthocyanin as a coloring component. As shown in FIG. 1, the structure of anthocyanin is a glycoside of anthocyanidin, which is the aglycon. Black currant anthocyanin is mainly composed of delphinidin and cyanidin as the anthocyanidin.

As J. Banaszczyk et al. have reported in Fruits Process 6(8), 321-325, 1996, the content of the black currant anthocyanin at Bx. 11 is not more than 600 to 800 mg/l regardless of variety. This indicates that 100% fresh juice of freshly-squeezed black currant contains only 0.06 to 0.08% by weight of black currant anthocyanin. Because the Bx of the juice is about 11, the content of black currant anthocyanin is 0.55 to 0.73% by weight on the basis of solid matters. According to this report, storage of the juice for 14 weeks decreases the amount of the black currant anthocyanin to 300 mg/l. Further, the content of the black currant anthocyanin greatly varies depending on crop year. By the subsequent year, content decreased to 80 mg/l, that is, one tenth of the previous year (0.07% by weight on the basis of solid matters). As indicated above, the amount of the black currant anthocyanin in the fresh black currant juice greatly varies depending on the storage condition and crop year, i.e., 0.07 to 0.73% by weight on the basis of solid matters. This indicates that foods containing 1% or more by weight of black currant anthocyanin on the basis of solid matters did not exist. Furthermore, black currant 100% fruit juice is not suitable for drinking due to its extreme acidity so that a neutralizer, a sweetener and the like are usually added to the juice. For this reason, the amount of the black currant juice added in the actual production of juice is generally much less. For general quaffable black currant juice, the content of black currant anthocyanin is generally not more than 0.5% by weight on the basis of solid matters although it depends on the amount of neutralizer or sweetener added. Thus, the content of black currant anthocyanin in conventional foods derived from black currant was not more than 0.73% by weight on the basis of solid matters, not more than 0.08% by weight on a product basis, for the 100% fruit juice which was unsuitable for drinking, and not more than 0.5% by weight on the basis of solid matters for general quaffable juice.

Jams are produced by using frozen fruit as starting materials with the addition of a large quantity of, for example, sugar and pectin. Therefore, in general, the content of black currant anthocyanin is up to about 0.3% by weight on the basis of solid matters, and up to about 0.2% by weight on a product basis. It is a matter of course that the content of organic acids and sugar is larger than usual fruit juice.

"Explanatory notes on the list of food additives other than chemically synthesized products" describes a coloring agent of black currant although it is hardly commercially available these days. According to this, the coloring agent is produced by "squeezing from black currant belonging to family saxifraga or extracting with the aid of water". This coloring agent is produced merely by extraction, and the content of black currant anthocyanin, organic acids, and the saccharide content is equivalent to those of general fruit juice. Properties thereof are described as "red to dark red or dark blue liquid or a paste or a powder", indicating that a powdery coloring agent existed. However, this powdery coloring agent is also produced by pulverizing the liquid coloring agent obtained by extraction with the addition a binder and the like. Regarding the black currant anthocyanin component on the basis of solid matters, this is equal to or less than that of fresh fruit juice.

Conventionally, anthocyanin has had a problem in its stability, that is, it decomposes when the fruit juice is used in drinks such as juice.

Fruits containing a large quantity of anthocyanin include blueberries. Some varieties of blueberries contain not less than 2% by weight of blueberry anthocyanin on a dry fruit basis. Therefore, in some food industries, blueberry anthocyanin is extracted with the aid of an organic solvent and the like from, for example, fruits or fruit juice concentrate to utilize it as a coloring agent for foods ["Shokuhin kogyo (THE FOOD INDUSTRY)" issued Aug. 30, 1997].

Blueberry anthocyanin comprises: 5 kinds of anthocyanidins, i.e., cyanidin, peonidin, delphinidin, petunidine, and malvidin; and 15 types of anthocyanins, i.e., combinations of 3 types of sugar moieties, i.e., glucose, arabinose, and galactose. The main component is reported as malvidin, and the content of delphinidin and cyanidin is about 10 to 20% by weight ["Shokuhin to kaihatsu (up-to-date food processing) vol. 31, No. 3, p 5-8].

As described above, properties, hues, pharmacological functions and the like of blueberry anthocyanin would be different from those of black currant anthocyanin since anthocyanidin compositions contained therein differ significantly from one another.

Only an infinitesimal quantity of blueberry anthocyanin is needed for coloring. Therefore, currently employed coloring agents contain only about 2% by weight of the anthocyanin on the basis of solid matters, i.e., equivalent to fruit juice concentrate. Further, such coloring agents for foods are extracted with an organic medium so that a distinctive flavor thereof is lost.

The content of these blueberry anthocyanins is merely for use in coloring agents. Therefore, in for example drinks using a coloring agent extracted from blueberry described in Japanese Patent Laid-Open No. 84564/1997, the amount of the coloring agent added is 0.025 to 0.05% by weight, which is an infinitesimal quantity, 0.00625 to 0.0125% by weight, in terms of the amount of blueberry anthocyanin. Conventionally, foods containing a large quantity of blueberry anthocyanin did not exist.

As described above, the amount of black currant anthocyanin contained in black currant is very small, not more than about 0.7% by weight on the basis of solid matters. Black currant anthocyanin has hitherto been regarded unsuitable as a starting material for a coloring agent. Thus, it is a matter of course that there was no food containing a large quantity of black currant anthocyanin. For this reason, a black currant anthocyanin material, which can be added to food in a large amount, has been strongly desired.

In Europe, blueberry anthocyanin has hitherto been employed as a pharmaceutical. However, anthocyanin derived from other fruits was not very well known possibly because of its anthocyanin content.

When blueberry anthocyanin is employed as a pharmaceutical, a larger quantity of the anthocyanin has to be taken compared to the case where blueberry anthocyanin is employed as a coloring agent. Therefore, anthocyanin has to be purified, and a process therefor is disclosed in, for example, Japanese Patent Laid-Open No. 99090/1991. Disclosed therein is a process wherein an aqueous solution containing a bisulfite ion prepared by adding sulfur dioxide, sodium hydrogensulfite, sodium pyrohydrogensulfite and the like is added to a fruit or an extract thereof, separation is performed using a nonionic polymeric resin under neutral pH conditions, sulfurous acid is eliminated using an inert gas, and anthocyanin is then extracted with an organic medium immiscible with water (for example, butanol and amyl alcohol). However, this process is not directed to food applications but to pharmaceutical and cosmetic applications. In Japan, however, the Food Sanitation Law prohibits the use of organic media such as butanol and amyl alcohol, and thus, they cannot be used for foods. Use of harmful sulfurous acid gas (described in vol. 3 of "Dictionary of Biochemistry", NIHON KAGAKU DOJIN) is not preferable for fear of its remaining in products. Therefore, the anthocyanin according to Japanese Patent Laid-Open No. 99090/1991 was only applicable for pharmaceuticals, but not applicable for foods. This had led to the need of compositions for foods containing a large quantity of anthocyanin in the food industry.

Japanese Patent Publication No. 50633/1983 describes a process for producing anthocyanin for foods. This process exemplifies grapes or products obtained from grapes, and is carried out by a combination of an ultrafilter membrane having a cutoff point in the range of a molecular weight of 1,000 to 70,000, at a molecular weight of about 20,000 under optimal conditions, with an uncharged reverse osmosis membrane having salt retention rate of 30 to 99%, preferably 50 to 90% in the case of NaCl. Reverse osmosis membranes used in this process are of an uncharged type, the salt retention rate thereof is greatly different from that of the present invention, and the membrane is used for separation of water only, thus this process greatly differs from the process of the present invention. In the examples, extraction is carried out with a solution containing sulfurous acid anhydride and alcohol. In actual operation, use of an organic medium and evolution of sulfur dioxide is of concern. According to measurement of the optical density of anthocyanin, when the ultrafilter membrane is utilized, optical density is concentrated from 7,150 to 15,020, i.e., a concentration factor of 2.1 times compared to before filtration. When the uncharged reverse osmosis membrane is utilized, optical density is concentrated from 7,150 to 7,400, i.e., the concentration factor of 1.03 times compared to before filtration. This indicates that the ratio of concentration and purification is low. There is no description on the content of grape anthocyanin. However, even if an assumption is made that the content of grape anthocyanin in fruit juice before purification is 0.5% by weight on the basis of solid matters, according to the process in Japanese Patent Publication No. 50633/1983, the content of the grape anthocyanin in the extract obtained by ultrafiltration after purification is 1.05% by weight, and the content of grape anthocyanin in the concentrate obtained through the uncharged reverse osmosis membrane is about 0.52% by weight on the basis of solid matters. This indicates that the content is not high, and the quality is unsatisfactory.

According to the process disclosed in Japanese Patent Publication No. 31225/1985, anthocyanin is extracted with the aid of a sulfur dioxide solution from grapes, cranberries, blackberries and the like and separated by ultrafiltration. As described in Example 1 of the publication, in this process, 200 to 500 ppm of sulfur dioxide (sulfurous acid gas) remains in the final product. According to this process, the anthocyanin content of the final product is described to be about 1.0% by weight.

Japanese Patent Laid-Open No. 223756/1984 describes a process wherein anthocyanin is purified using an ion-exchange resin or an absorptive resin. However, there is no description on the concentration of anthocyanin in the prepared coloring matter. The purification process is directed to the removal of sludge generated in drinks.

Starting materials for anthocyanin described in these known documents are mostly blueberries (Bilberry, *Vaccinium. myrtillus*) which contain a large quantity of anthocyanin in the fruit thereof, or grapes which are inexpensive as fruits. There is no description concerning black currant.

The present inventors have keenly searched for a process for producing compositions for foods containing a large quantity of black currant anthocyanin without using harmful substances and found an effective process for the first time.

Surprisingly, foods and drinks, comprising the black currant anthocyanin produced according to this process, have visual function improvement effect, blood fluidity improvement function, and blood pressure lowering function. They are found to be effective as functional foods and drinks.

Visual functions are important functions accounting for a large part of sensory function. However, lowered visual function has become a problem these days. For those who operate computers and the like including personal computers and word processors, it is widely known that the rate of complaints of asthenopia is significantly higher than those who do not operate computers.

In optic organs, continuous operations concentrating on near points including computer work and computer games, maintain stress on the ciliary muscle which is a smooth muscle. This leads to reflact value of myopia, that is, pseudomyopia. This is reported in Japanese Journal of Ophthalmology, 72, 2083-2150 (1968). It is an established theory that this pseudomyopia some day becomes myopia. Substances for preventing or improving lowered refracting power of crystalline lens or pseudomyopia caused by computer operations are required.

As the number of senior citizens increases in society, the problem of lowered visual acuity in senior citizens is growing. In our daily lives, there has been a rapid increase in situations where there are complaints of lowered visual acuity. For example, as the number of senior drivers rapidly increases, the occurrence of problems, for example, dazzling going into or out of tunnels and lowered visual acuity at night which are problems not associated with young drivers, has become significant.

On the other hand, many people commonly use eyeglasses and contact lenses to correct their visual acuity. The use thereof, however, is inconvenient in their lives. In particular, people, who suffer from myopia in combination with presbyopia, astigmatism or the like, have serious inconveniences so many people hope for recovery of function.

Conventionally, attempts have been made at curative mechanisms for the improvement or recovery of visual function by utilizing visual acuity recovery training such as watching distant points, surgery, pharmaceuticals and the like. None of these processes, however, is very common.

Several studies have been already made on pharmaceuticals having a visual function improvement or recovery function. For example, phosphoramidon is the subject of a patent application as an endothelin converting enzyme inhibitor having curative effects on asthenopia (Japanese Patent Laid-Open No. 143099/1997). For example, taurine, menthol, neostigmine methylsulfate, and VE acetate are subjects of a patent application as instillations for improving asthenopia (Japanese Patent Laid-Open No. 143064/1997). Also subjects of patent applications are, for example, an emollient for strain of ciliary muscle (Japanese Patent Laid-Open No. 133225/1995), a therapeutic agent for asthenopia using cyclopentolate hydrochloride (Japanese Patent Laid-Open No. 149517/1990), and a solid pharmaceutical using adenosine sodium triphosphate (Japanese Patent Laid-Open No. 308232/1989). Most of these substances, however, are instillations that are pharmaceuticals used as eye drops. Although administration of these pharmaceuticals can temporarily relieve symptoms, chronic symptoms would not be relieved. Therefore, substances having effects on improving visual function or substances for preventing the lowering of visual function through routine food ingestion are desired. In fact, there are several reports on foods functioning to improve visual function. However, effects were measured only for subjective symptom so that scientific and objective evaluation of effects using equipments has not been carried out. For example, a triglyceride comprising docosahexaenoic acid, α-linolenic acid, and γ-linolenic acid is reported in Japanese Patent Laid-Open No. 255417/1995 wherein the evaluation is carried out by merely questioning the subjects in respect of their subjective symptoms in which subjects are simply divided into two groups to conduct a test. Therefore, individual differences among subjects are likely to develop. Also, because the number of participants "n" is as small as 5, and statistical processing is not particularly conducted, actual effects cannot be said to have been scientifically evaluated.

Regarding substances for maintaining eye function, those containing a viscera concentrate of mirror carp, a ginseng extract, Pseudoginseng, powders of pearl shell, a chrysanthemum, and a cassia seed extract described in Japanese Patent Laid-Open No. 97690/1993, supposedly have effects. Substances that are supposed to be active ingredients include a wide variety of substances and their effects are not specified. According to the examples in the publication, since the evaluation was made only by a questionnaire, it is hard to say the effects are scientifically verified.

In Japanese Patent Laid-Open No. 97691/1993, compositions having functions for improving eye diseases and functions for maintaining eye mechanisms are subject of a patent application, and proposed active substances include a shark fin extract, a viscera concentrate of mirror carp, a ginseng extract, Pseudoginseng, powders of pearl shell, chrysanthemum, a Chinese matrimony vine extract, and a cassia seed extract. These proposed substances lack scientific grounds as with the previously described publication.

Also subjects of patent applications as products, having functions for recovering visual acuity, are health foods for eyes comprising, as essential ingredients, the leaf portion of Japanese persimmon and the fruit of guava, as described in Japanese Patent Laid-Open No. 59217/1987. According to this invention, as with the above-described invention, the visual acuity is subjectively examined and effects are hardly scientifically verified.

Food materials having mechanisms for improving visual function, which are recently gaining people's attention, include the blueberry. According to this report, a double blind cross over experiment for a group comparison test is carried out for 20 patients who have subjective symptoms of mental fatigue and asthenopia with the control group being provided with a placebo. Unlike the evaluation process of foods cited in the above-described literature, an evaluation using equipment is additionally carried out. The results thereof show an improvement in subjective symptoms and in a flicker test. However, the results show no improvement in: for example, subjective epidoptometry, i.e., 30 cm visual acuity and 5 m visual acuity; and objective epidoptometry, i.e., a measurement of refracting power "THE FOOD INDUSTRY" issued Aug. 30, 1998). Further, the flicker which is the equipment used is described in The Journal of Japan Accident Medical Association, 1992, vol. 40, No. 1, p. 12-15: "a flicker test is a process for evaluating asthenopia and is related to fatigue in brain cortex, and cerebral excitability, but not related to an optic center". According to the description on page 221 of "Practical Ophthalmology" vol. 18, issued by Bunkodo, "a measurement of central flicker is effective in evaluating a disorder of tertiary neuron such as ophthalmic nerve disease, (omitted), the flicker is unaffected by refractive error or mild optic media". The flicker test measures cerebral functions rather than visual functions. More specifically, regarding the effect of blueberries, the evaluation is presumably made on the effect attained by recovery of central function, in particular, cerebral function rather than improvement of visual function.

As described above, no food materials have hitherto been known where an effect on improving the visual function was scientifically verified using proper equipment.

The present inventors have found that foods, containing black currant anthocyanin for foods purified by the process described below, have scientifically verified mechanisms for improving visual function.

Anthocyanidins, being aglycon of anthocyanin, have been employed as pharmaceuticals in Europe, and are known to have pharmacological properties valuable in treating peripheral vascular disease (Japanese Patent Laid-Open No. 81220/1991). However, those having a scientifically verified visual function improvement effect have not been developed as foods.

Starting materials for anthocyanin described in patent specifications for pharmaceuticals containing anthocyanin are mostly blueberries (Bilberry, *Vaccinium. myrtillus*) which contain a large quantity of anthocyanin in the fruit thereof or grapes which are inexpensive as fruit. The black currant has not been employed. Therefore, pharmacological effects of black currant anthocyanin have been hardly studied at all. This may be because the content of black currant anthocyanin in black currant is a very small quantity of not more than about 0.7% by weight on the basis of solid matters. The present inventors have found a novel function of black currant anthocyanin, which has hitherto been left out of account. Because the blueberry anthocyanin affects the central nerves rather than visual function, functions and mechanisms thereof could be different from those of black currant anthocyanin.

In recent years, the spread of life-style related diseases, attributable to opulence and lack of exercise, has come to be regarded as a problem, and particularly, matters associated with the circulatory system such as an elevated blood pressure, hyperglycemia, and an increase in neutral fat and cholesterol in blood have come to be regarded as serious. In particular, adverse affects created by neutral fats and cholesterol cause an increase in blood viscosity, thereby preventing blood from rapidly flowing through blood vessels. This increases vascular resistance which may in turn cause the elevated blood pressure. It is known that, as a problem of blood cells, for example, lowered deformability of human red blood cells, an improvement in leukocyte adhesiveness, and exaltation in platelet aggregation activity lower blood fluidity.

Currently, pharmaceuticals for accelerating the metabolism of neutral fats or the cholesterol are available, however, satisfactory effects are not provided. Due to the fact that these are pharmaceuticals, there is also the problem of side effects. As with the foods derived from *Physalis angulata* L. according to Japanese Patent Laid-Open No. 143324/1986 for improving the levels of blood pressure and blood sugar, there has been a report on foods having a function of relaxing vasoconstriction and dilating peripheral vessels. However, temporary relaxation of vasoconstriction only provides a temporary solution and would conversely lead to deterioration of peripheral vessels. Thus, foods which would affect blood itself to improve its fluidity, thereby preventing diseases such as elevated blood pressure, cerebral hemorrhage, and coronary artery disease, have long been sought.

Conventional substances having a function for improving blood fluidity include the following pharmaceuticals. Japanese Patent Laid-Open No. 43436/1999 describes tocopherol phosphoric ester as a preventive and a therapeutic agent for peripheral vascular flow disorder. Japanese Patent Laid-Open No. 77328/1987 describes anthocyanin or anthocyanidin derived from crown of thorns, as a circulation-improving-agent which has a function of dilating blood vessels which acts as a diuretic, and acts to dilate coronary vessels, and improving cerebral circulation.

Japanese Patent Laid-Open No. 147523/1998 describes pharmaceuticals or foods containing a γ-linolenic acid as an active ingredient which acts to improve blood fluidity. The invention according to the above-described publication is carried out using equipment to directly measure blood fluidity as with the process adopted by the present inventors. This equipment enables direct observation and measurement of the condition of blood fluidity under a CCD camera by employing MC FAN KH-3 (Hitachi Haramachi Electronics Co., Ltd.). According to the examples of the publication, however, the efficacy of γ-linolenic acid is attained by administration thereof for two months to patients undergoing a dialysis treatment, and the γ-linolenic acid is used pharmaceutically.

Japanese Patent Laid-Open No. 81220/1991 describes a reduction of permeability of ciliary vessels by anthocyanidin. This is a pharmaceutical employed for treating diseases in peripheral vessels and is mainly related to effects on blood vessels. Conventionally, there is no description regarding the effects of anthocyanin or anthocyanidin on, for example, erythrocytes, leukocytes, and platelets in blood. There is no description regarding black currant, either.

On the other hand, known conventional foods for improving blood fluidity, include encapsulated foods according to Japanese Patent No. 2801990 which are provided by the addition of at least one member selected from the group consisting of an edible fatty oil, vitamin E, and lecithin to lipids surrounding the internal organ of *Laticauda semifasciata*. However, this patent is limited to encapsulated foods and not applicable to other types of foods. Also in this patent, a process is adopted wherein renal plasma flow is measured by a paraaminohippuric acid process to estimate the function of peripheral vessels. Effects thereof are limited to a function of improving peripheral blood fluidity.

Japanese Patent Laid-Open No. 112077/1996 describes that compositions for health foods derived from chitosan and a ginkgo leaf extract are effective in improving peripheral blood fluidity in the brain although there is no detailed description. Also, Japanese Patent Laid-Open No. 257866/1998 describes a health food comprising myo-inositol and the ginkgo leaf extract therein although detailed study thereof is not additionally described.

Japanese Patent Laid-Open No. 287576/1998 describes that a saffron extract acts to improve peripheral blood stream. Peripheral resistance of the blood stream is measured using a chart of Korotkoff's sounds and the effect thereof is limited to an effect of improving peripheral blood fluidity.

As described above, in the field of these foods, there has been no description on black currant anthocyanin in relation to blood fluidity improvement effect or blood pressure lowering effect.

In addition, administration of pharmaceuticals enables temporary recovery in visual function improvement effect, blood fluidity improvement function, blood pressure lowering function, etc. However, this does not relieve chronic symptoms. Therefore, substances have been desired in which visual functions, blood fluidity, and blood pressure are improved through the routine ingestion of foods. As described above, the content of black currant anthocyanin in black currant is in a very small quantity of not more than about 0.7% by weight on the basis of solid matters. Thus, foods containing a large quantity of black currant anthocyanin have not existed. Therefore, strongly desired was a black currant anthocyanin material, which can be added to foods in a large quantity. The process of the present invention provides a highly concentrated anthocyanin composition, which can be added to foods. This enables the addition of a large quantity of black currant anthocyanin to general foods. The present invention enables, for the first time, the routine ingestion of foods to improve visual function, foods to improve blood fluidity, or foods that function to lower blood pressure, respectively containing a large amount of black currant anthocyanin. According to the present invention, pharmacological functions of black currant anthocyanin, for example, prevention of chronic visual function deficiency and the like, effects in improving visual function, or a function for improving blood fluidity, and a function for lowering blood pressure are continuously realized by ingesting anthocyanin as foods.

Unexpectedly, the highly concentrated anthocyanin composition according to the present invention, unlike conventional fruit juice, has excellent stability and thus, is able to be stored for a long period of time when employed in drinks such as juice.

SUMMARY OF THE INVENTION

As described above, conventional substances for foods containing black currant anthocyanin derived from black currant include black currant juice concentrate and black currant pigment. However, since the content of black currant anthocyanin in black currant juice concentrate is about 0.5% by weight, as much as 20 g of juice concentrate should be formulated to ingest 100 mg of the black currant anthocyanin. In this case, however, 4 to 6 g of an organic acid, which coexists therein, is added together so that the acidity is too strong to incorporate the black currant anthocyanin into general foods. Due to the fact that black currant pigment generally contains not more than 0.7% by weight of black currant anthocyanin, 14 g of the pigment (14% by weight in terms of 100 g of foods) should be incorporated to ingest 100 mg of black currant anthocyanin. In general foods, the amount of pigment incorporated is not more than 0.1% by weight so that the actual incorporation thereof was difficult.

Conventionally, the juice concentrate and pigment had poor stability, and thus, it was impossible to store for a long period of time when fruit juice is used in drinks such as juice.

For this reason, it has hitherto been difficult to develop health foods which, while preserving the distinctive flavor of black currant, at the same time impart effects of the black currant anthocyanin. Therefore, the present inventors have studied and found an effective process for purifying black currant anthocyanin which is applicable for foods.

In addition, the highly-concentrated anthocyanin composition thus obtained is, unlike conventional fruit juice, excellent in stability so that it could be stored for a long period of time when used in drinks such as juice.

In contrast, as described above, substances were desired wherein an improvement in visual function is realized through the routine ingestion of foods. Therefore, the inventors have sought food materials, the effects of which can be scientifically verified by objective evaluation utilizing proper equipments, in addition to subjective measurement, that can be continuously ingested as foods, and have effects on improving visual functions. This was led to the discovery of effective compositions.

The present inventors have found that the composition has an effect of improving blood fluidity as well as an effect of lowering blood pressure.

The object of the present invention is to provide composition for foods containing a large quantity of black currant anthocyanin, a process for producing the same without using harmful substances such as an organic solvent, and functional foods and drinks having a visual function improvement effect, blood fluidity improvement function, and blood pressure lowering function.

In order to attain the above object, the present inventors have keenly studied, and as a result, they succeeded in the efficient purification and separation of black currant anthocyanin without using sulfurous acid gas or an organic solvent which is harmful on human body, by performing membrane separation with a charged reverse osmosis membrane. Thus, the present inventors have succeeded for the first time in the production of compositions for foods containing a large quantity of black currant anthocyanin. By this process, compositions for foods containing a large quantity of black currant anthocyanin were produced in which not less than 1.0% by weight of black currant anthocyanin, not less than 0.5% by weight of a delphinidin glycoside, and not less than 0.4% by weight of delphinidin-3-o-rutinoside were contained. These compositions contain a large quantity of black currant anthocyanin, have adequate acidity, and nevertheless have the distinctive flavor of the black currant. Therefore, these compositions are suitable for application in various foods. Further, the present inventors have found for the first time that, in a group of foods and drinks incorporating the compositions containing a large quantity of black currant anthocyanin therein, several effects of improving visual function, blood fluidity improvement function, and blood pressure lowering function.

More specifically, the present invention provides compositions for foods containing a black currant anthocyanin comprising 1 to 25% by weight, preferably 5 to 25% by weight of black currant anthocyanin on the basis of solid matters. The black currant anthocyanin includes those obtained through purification and concentration of black currant juice using a charged reverse osmosis membrane.

Further, the present invention provides compositions for foods containing a black currant anthocyanin characterized in that the black currant anthocyanin comprises delphinidin wherein the content of the delphinidin glycoside is 0.5 to 12.5% by weight, preferably 2.5 to 12.5% by weight, on the basis of solid matters.

Furthermore, the present invention provides compositions for foods containing a black currant anthocyanin characterized in that the black currant anthocyanin comprises delphinidin-3-o-rutinoside wherein the delphinidin-3-o-rutinoside content is 0.4 to 10% by weight, preferably 2 to 10% by weight, on the basis of solid matters.

Still further, the present invention provides a process for producing compositions for foods containing a black currant anthocyanin characterized in that black currant juice, as a starting material, is purified and concentrated using a charged reverse osmosis membrane. The charged reverse osmosis membrane includes a negatively charged reverse osmosis membrane. Preferably, the negatively charged reverse osmosis membrane has salt retention rate of 5 to 20% in the case of NaCl.

The present invention further provides a process for producing compositions for foods containing a black currant anthocyanin characterized in that black currant juice, as a starting material, is purified and concentrated by utilizing a charged reverse osmosis membrane and an ion-exchange resin. The ion-exchange resin includes a strong acid cation-exchange resin.

The present invention still further provides functional foods and drinks comprising the above-described compositions for foods. The foods and drinks include candies, chewing gums, juice, chocolates, tablets, gelatinous foods, and jams.

The present invention provides the above compositions for foods and functional foods and drinks characterized by having a visual function improvement effect. The visual function improvement effect includes an sthenopia recovery function, a recovery of lowered visual acuity function, a myopia recovery function, a recovery of lowered-refracting power of the crystalline lens function, a visual acuity in darkness improvement function, darkness adaptation improvement function, retinal function improving function, and retinal rods improvement function.

The present invention provides the above compositions for foods and functional foods and drinks characterized by having blood fluidity improvement function and blood pressure lowering function.

BRIEF DESCRIPTION OF DRAWINGS

FIG. 2 shows effects on improvement in adaptation to darkness attained by ingesting black currant anthocyanin.

BEST MODE TO CARRY OUT THE INVENTION

Figure 1:
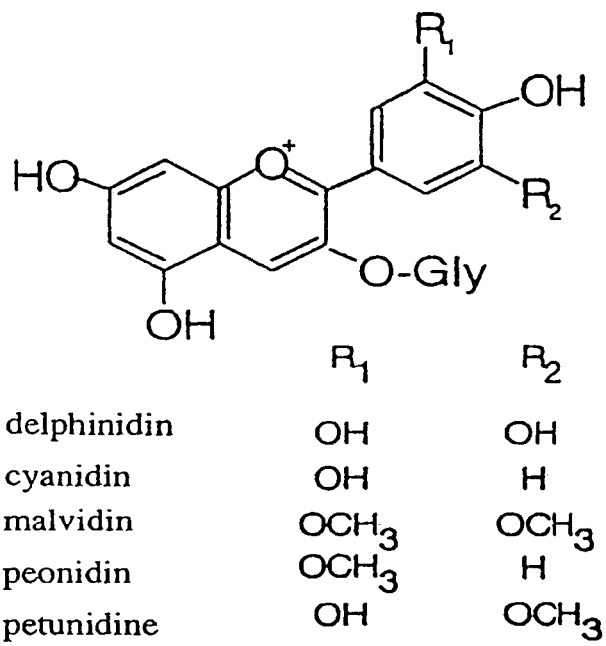
FIG. 1 shows a chemical structure of anthocyanin.

According to the present invention, compositions for foods containing a large quantity of black currant anthocyanin are produced by performing membrane separation using a charged reverse osmosis membrane to efficiently purify and concentrate black currant anthocyanin without the use of, for example, harmful sulfurous acid gas or organic solvents.

The black currant anthocyanin according to the present invention refers to an anthocyanin extracted from black currant fruit or black currant juice concentrate. A delphinidin glycoside includes delphinidin-3-o-rutinoside and delphinidin-3-o-glucoside in addition to delphinidin.

The content of black currant anthocyanins described below is measured as follows. The main component of black currant anthocyanin is, as shown in Table 1, delphinidin-3-o-rutinoside, delphinidin-3-o-glucoside, cyanidin-3-o-rutinoside, and cyanidin-3-o-glucoside.

TABLE 1

Content of anthocyanin component in each fruit juice concentrate

| | Blueberry anthocyanin | Black currant anthocyanin | Black chokeberry anthocyanin |
|---|---|---|---|
| Delphinidin glycoside | 35.1% | 67.0% | 0.0% |
| Delphinidin | 0.6% | | |
| Delphinidin-3-o-galactoside | 12.0% | | |
| Delphinidin-3-o-glucoside | 12.3% | 12.8% | |
| Delphinidin-3-o-rutinoside | 0.0% | 54.2% | |
| Delphinidin-3-o-arabinoside | 10.2% | | |
| Cyanidin glycoside | 29.7% | 30.0% | 100.0% |
| Cyanidin | 0.0% | | |
| Cyanidin-3-o-galactoside | 11.0% | | 65.4% |
| Cyanidin-3-o-glucoside | 11.1% | 3.6% | 3.9% |
| Cyanidin-3-o-rutinoside | 0.0% | 29.3% | |
| Cyanidin-3-o-arabinoside | 7.6% | | 27.6% |
| Cyanidin-3-o-xyloside | | | 3.1% |
| Malvidin glycoside | 10.4% | 0.0% | 0.0% |
| Malvidin | 0.0% | | |
| Malvidin-3-o-galactoside | 2.4% | | |
| Malvidin-3-o-glucoside | 6.5% | | |
| Malvidin-3-o-rutinoside | 0.0% | | |
| Malvidin-3-o-arabinoside | 1.5% | | |
| Peonidin glycoside | 10.9% | 0.0% | 0.0% |

TABLE 1-continued

Content of anthocyanin component in each fruit juice concentrate

| | Blueberry anthocyanin | Black currant anthocyanin | Black chokeberry anthocyanin |
|---|---|---|---|
| Peonidin | 0.0% | | |
| Peonidin-3-o-galactoside | 2.1% | | |
| Peonidin-3-o-glucoside | 7.6% | | |
| Peonidin-3-o-rutinoside | 0.0% | | |
| Peonidin-3-o-arabinoside | 1.2% | | |
| Petunidine glycoside | 13.9% | 0.0% | 0.0% |
| Petunidine | 0.0% | | |
| Petunidine-3-o-galactoside | 3.9% | | |
| Petunidine-3-o-glucoside | 7.5% | | |
| Petunidine-3-o-rutinoside | 0.0% | | |
| Petunidine-3-o-arabinoside | 2.5% | | |

These samples were subjected to an HPLC analysis to measure the response coefficient (mg/peak area) for each sample at 520 nm, which is a main region where an anthocyanin develops color. The sample, the black currant anthocyanin content of which is to be measured, is subjected to HPLC analysis and the content is determined as follows. The peak area of each component is multiplied by the response coefficient obtained from samples, thereby calculating the content of each component. The calculated value is then compared to the amount injected, thereby calculating the content on the basis of % by weight. Therefore, the content of black currant anthocyanin includes the amount of sugar moiety bonded as well as the amount of anthocyanidin as an aglycon. Likewise, the delphinidin content includes the amount of sugar moiety bonded to delphinidin as well as the amount of delphinidin as the aglycon. This is also true of blueberry anthocyanin and black chokeberry anthocyanin.

The charged reverse osmosis membrane used in the present invention greatly differs from the conventional membrane used in the process described in, for example, Japanese Patent Publication No. 50633/1983. More specifically, the uncharged reverse osmosis membrane used in the process according to Japanese Patent Publication No. 50633/1983 has retention rate of 30 to 99%, preferably 50 to 90% in the case of NaCl and sugar retention rate of 90 to 100%. This indicates that this membrane retains low molecular-weight substances such as sugar and acid while discharging water only.

In contrast, the charged reverse osmosis membrane used in the present invention is negatively charged. Further, the membrane with the retention rate of about 5 to 20%, preferably about 10%, in the case of NaCl efficiently removes monosaccharides and organic acids, and thus, it was optimal for separation and purification of the black currant anthocyanins. This membrane originally has a fractionated molecular weight of about 2,000 to 3,000, and thus, the black currant anthocyanin with a molecular weight of 500 to 1,000 is expected to pass therethrough. Also, since this membrane is of a negatively charged type, positively charged substances such as black currant anthocyanin were expected to be adsorbed thereon.

However, as described in Example 1 below, when black currant anthocyanin is concentrated using this type of membrane, a large part of the black currant anthocyanin is, surprisingly, retained without being passed through. Sugar, organic acids and the like, which account for a large part of other ingredients are removed at the same time water is removed, thereby concentrating black currant anthocyanin. The solution thus concentrated has a flavor distinctive to black currant. According to the results of HPLC analysis, the content of black currant anthocyanin is not less than 1% by weight on the basis of solid matters (6.4% by weight in the case of a concentrate, 5.1% by weight after pulverization) and the organic acid content is not more than 5% by weight, but monosaccharide was not found. This indicates that this concentrate is low in acidity and sweetness, and thus, any type of flavor could be imparted thereto. Therefore, this concentrate could be incorporated in any type of food, and thus, is extraordinarily excellent as starting materials for foods. As described above, the amount of black currant anthocyanin in black currant juice as a starting material greatly varies. Therefore, purification and concentration can be carried out from various starting materials in an equivalent manner to prepare compositions containing a large quantity of black currant anthocyanin as shown in Table 3. Regardless of the test group, the concentration factor of anthocyanin is increased by about 8 to 15 times, and the content of sugar and organic acid in the composition is low. As described in Example 2, this composition could be further subjected to separation by chromatography to increase the concentration factor by about 4 times while achieving a purity of 25%.

The formulation analysis of black currant anthocyanin in these compositions shows that the main ingredient is 50.4% by weight of delphinidin-3-o-rutinoside (on the basis of solid matters, 3.2% by weight in a concentrate, 2.6% by weight after pulverization). This ingredient is not present in other berries such as blueberries. Anthocyanidin as the aglycon comprises 61.2% by weight of delphinidin (on the basis of solid matters, 3.9% by weight in a concentrate, 3.1% by weight after pulverization), 38.8% by weight of cyanidin (on the basis of solid matters, 2.5% by weight in the concentrate, 2.0% by weight after pulverization), with the main ingredient being delphinidin.

According to "Shokuhin to kaihatsu (up-to-date food processing)" vol. 31, No. 3, p 5-8, the blueberry comprises 5 types of aglycons, i.e., cyanidin, peonidin, delphinidin, petunidine, and malvidin, and 15 types of anthocyanins being combinations of these with 3 types of sugar moieties, i.e., glucose, arabinose, and galactose. The main ingredient is reported as malvidin, and the content of delphinidin is about 20% by weight. Black currant anthocyanin comprises, as a main ingredient, delphinidin which is contained in an amount of not less than 50% by weight in anthocyanin. Since it comprises delphinidin-3-o-rutinoside as a main ingredient which is absent in other berries, it greatly differs from other berry anthocyanins such as blueberry anthocyanin. This is as shown in the compositions (concentrate, pulverized) prepared in Examples 1 and 2 described below.

Thus, the composition according to the present invention could be in the form of, for example, a paste or gel in addition to a liquid or solid such as a powder as described in Examples 1 and 2.

Using the powder and the concentrate described in Examples 1 and 2, a test was carried out by incorporating anthocyanin into foods with a process described in Examples 3 to 11. This test provided good results. The content of each black currant anthocyanin component in these examples is summarized in Table 2.

TABLE 2

Content of anthocyanin component in each sample

| | Concentration on solid basis (BX) | Content on product basis Anthocyanin | Content on solid basis | | | Content on anthocyanin basis | |
| --- | --- | --- | --- | --- | --- | --- | --- |
| | | | Anthocyanin | Delphinidin glycosides | Delphinidin-3-o-rutinoside | Delphinidin glycosides | Delphinidin-3-o-rutinoside |
| Fresh black currant juice | About 11 | Not more than 0.08 wt % | Not more than 0.73 wt % | Not more than 0.37 wt % | Not more than 0.29 wt % | Not less than about 50 wt % | Not less than about 40 wt % |
| Black currant juice concentrate | About 65 | Not more than 0.48 wt % | Not more than 0.73 wt % | Not more than 0.37 wt % | Not more than 0.29 wt % | Not less than about 50 wt % | Not less than about 40 wt % |
| Blueberry juice concentrate | About 65 | About 1.3 wt % | About 2 wt % | 0.4 wt % | 0 wt % | About 20 wt % | 0 wt % |
| Black chokeberry juice concentrate | About 65 | About 0.65 wt % | About 1 wt % | 0 wt % | 0 wt % | 0 wt % | 0 wt % |
| Commercially available black currant juice | About 11 | Not more than 0.08 wt % | Not more than 0.50 wt % | Not more than 0.25 wt % | Not more than 0.20 wt % | Not less than about 50 wt % | Not less than about 40 wt % |
| Commercially available black currant jam | About 90 | Not more than 0.2 wt % | Not more than 0.3 wt % | Not more than 0.15 wt % | Not more than 0.12 wt % | Not less than about 50 wt % | Not less than about 40 wt % |
| Concentrate obtained in Ex. 1 | About 65 | 4.16 wt % | 6.4 wt % | 3.9 wt % | 3.2 wt % | 61.2 wt % | 50.4 wt % |
| Powder obtained in Ex. 1 | 100 | 5.1 wt % | 5.1 wt % | 3.1 wt % | 2.6 wt % | 61.2 wt % | 50.4 wt % |
| Concentrate obtained in Ex. 2 (intermediate product) | 65 | 1.95 wt % | 3 wt % | 1.9 wt % | 1.6 wt % | 62.6 wt % | 52.8 wt % |
| Concentrate obtained in Ex. 2 | 65 | 16.25 wt % | 25 wt % | 15.7 wt % | 13.2 wt % | 62.6 wt % | 52.8 wt % |
| Powder obtained in Ex. 2 | 100 | 25 wt % | 25 wt % | 15.7 wt % | 13.2 wt % | 62.6 wt % | 52.8 wt % |

In contrast, with conventional processes using an ultrafilter membrane, the contemplated black currant anthocyanin could not be produced because the ultrafilter membrane had poor permeability, the content of the black currant anthocyanin as a concentrate was low, and concentration efficiency was poor.

As described in Example 13, compositions containing anthocyanin described in Examples 1 and 2 are, unlike conventional fruit juice, excellent in stability. Therefore, they could be utilized in drinks such as juice to be stored for a long period of time.

The present inventors have found effects of improving visual functions, especially effects on improving asthenopia in the compositions containing a large quantity of black currant anthocyanin.

Conventional processes for evaluating improvements, in visual function realized by pharmaceuticals, in cases such as asthenopia include various processes, for example, a process using a questionnaire to survey recovery from subjective sense of fatigue, a process measuring a constriction of bovine ciliary muscle, and a process measuring a refractive accommodation. The present inventors, however, adopted a VAS (visual analogue scale) as a process for subjectively measuring a level of asthenopia. This process has become increasingly employed these days in the evaluation of fatigue the reliability of which is supposedly relatively high. In the measurement, a 10 cm line without a scale is used with its left end representing a state without fatigue while the right end representing a state of utmost fatigue. Fatigue conditions of the subjects are plotted on the line to represent the level of fatigue by number obtained from the distance from the left end.

As a process for objectively determining the level of asthenopia, the present inventors had judged a process is optimal wherein the level of asthenopia is measured by employing an autorefractometer to measure the refracting power of the crystalline lens, and adopted this process. Originally, values indicating the refracting power of the crystalline lens (also referred to as a refraction value or a refraction level) objectively represent visual acuity, in particular, myopia and hypermetropia. In the Seminar on VDT Operation by Japan Society for Occupational Health, the examination of refraction using an autorefractometer and the like is recommended in addition to a general examination of central visual function for examination items associated with the visual acuity among visual function examination items. This is because ametropia is presumably in close relation with asthenopia. According to "Ganka (ophthalmology) MOOK, No. 23, 1985, Asthenopia, p. 10", it is described that "the refraction level of eyes should be especially important in the medical care of asthenopia. Sometimes asthenopia is completely cured by merely correcting the level of refraction. Also, in some cases, a correction of refraction more or less alleviates complains of asthenopia". It could be said that an improvement in the refraction value of the crystalline lens greatly affects myopia or pseudomyopia, and in turn asthenopia.

Processes for measuring refraction value are roughly classified into subjective measurements and objective measurements. Subjective measurements are processes which are generally employed at, for example, an eyeglass shop. In such a process, a subject wears a pair of eyeglasses with the lenses mounted thereon which are changed one by one. The refraction value at which a distant point can be seen well is determined as the refraction value of the subject. The value obtained by this process is inaccurate because it reflects the subject's will and the like. In the present application, therefore, an objective measurement, with higher accuracy, using an autorefractometer, is adopted. This process is carried out by, as a measuring principle, irradiating eyes with a near infrared beam to determine the refraction value from the level of divergence in an optical axis on the images of the reflected light from the retina.

In general, D (dioptor) represents the unit of refracting power. A general emmetrope has a refraction value of 0 D. For a person with myopia, the refraction value is shifted in a negative direction. In general, values up to −3 D indicate tenuis myopia, values from −3 D to −6 D a mild myopia, and values over −6 D excessive myopia. This is an inverse of the focal distance. That is, when the refraction value is −1 D, 1/1, this indicates that the maximum focal distance is only 1 m away from eyes. Likewise, when the refraction value is −5 D, 1/5, this indicates that the maximum focal distance is only 20 cm away from eyes.

Refraction value is supposedly associated with various parts in the eye tissues, such as, a tear layer, a cornea, an eye chamber, a crystalline lens, a vitreous body, an eye axis length, and a pupil diameter.

Adaptation to darkness described in the present invention refers to a process to increase the sensitivity for several ten minutes when eyes are moved from bright place to darkness. The retina senses the light, and the retina has two kinds of visual cells, i.e., rods and cones. The rods work for scotopic visual function and mainly control the light perception. The cones work for daylight visual function and mainly control color perception and form perception. For adaptation to darkness, both cones and rods are involved, and the adaptation realized by cones reaches its threshold in 5 to 10 min which corresponds to a process for regenerating the photo pigment in the cones. The adaptation realized by the rods reaches its threshold in 30 min. The point where the adaptation to darkness realized by the cones switches to the adaptation to darkness realized by rods is referred to as the Kohlrausch point. A lowering of adaptation to darkness results in night blindness or lowered visual acuity in darkness, i.e., sightlessness in darkness, or dazzlement in a bright place. Improvement in adaptation to darkness may have effects on the prevention of lowering in visual acuity in darkness, on the improvement of night visual function, on dazzlement and the like.

In the present invention, as described in detail in Example 3, a test on the effects on the improvement in asthenopia is carried out by artificially imparting asthenopia to the subjects due to computer operations and, prior to the conduct of operations, providing three types of juice-like drinks respectively containing black currant anthocyanin, blueberry anthocyanin, and black chokeberry anthocyanin in a large amount, measuring the refraction values after the application of operations, and then comparing the obtained values with the values before ingestion. The examination utilizing the above-described VAS is also carried out to subjectively test asthenopia. In the VAS examination, values obtained before ingestion were compared with those obtained after conduct of operations to examine the test group with the weakest level of fatigue. As a result, for 5 out of 10 subjects, ingestion of the black currant anthocyanin was most effective, for 3 subjects, blueberry anthocyanin was most effective, for 1 subject, black chokeberry anthocyanin was most effective, and 1 subject in the control group without digestion. The black currant anthocyanin was confirmed as most effective in improving asthenopia from the subjective examination. As a result of the measurement of refraction values, only the group which ingested the black currant anthocyanin showed significant effects in improving refraction values. The average of the refraction value of the dominant eye shows an improvement effect of 0.47 D. An improvement of 0.5 D in refraction value refers to an improvement effect by 2 grades in the level of myopia in eyeglasses. It is apparent that black currant anthocyanin has a great effect on the prevention of, or recovery from lowered visual acuity, and in particular, has an effect on the prevention of, or recovery from myopia. As described above, the refraction value is closely related to asthenopia. The recovery from asthenopia by recovering of refraction value can be greatly realized. The ingestion of black currant anthocyanin results in the recovery from, or prevention of asthenopia. This is also verified by objective examination.

In the test described in Example 3, the refraction value of the crystalline lens is measured at the site for relaxation of accommodation. The measurement demonstrates that black currant anthocyanin presumably realizes its improving effects by affecting the crystalline lens or the ciliary body having a function to control the thickness of the crystalline lens.

In addition, as described in Example 3, the improving effect in the refraction value is seen only in the black currant anthocyanin. This effect was not seen in the blueberry anthocyanin or black chokeberry anthocyanin an examination of which was simultaneously examined. The ingredients of each anthocyanin were shown in Table 1. As is apparent from this, the main ingredient of the black currant anthocyanin is delphinidin-3-o-rutinoside which is not contained in the other two anthocyanins. Differences in improving effects suggest that the delphinidin-3-o-rutinoside may be the active ingredient.

In the present invention, a group of foods incorporating compositions which contain a large quantity of black currant anthocyanin is prepared as described in Examples 5 to 11 in addition to juice-like drinks. Then, it is confirmed that this group of foods has an effect on improving visual function, that is, the foods in the group are functional foods. For the group of foods described in Examples 3 to 11, foods containing a large quantity of black currant anthocyanin could not be produced from conventional fresh juice or black currant juice concentrate. However, the utilization of the compositions containing a large quantity of black currant anthocyanin according to the present invention enabled, for the first time, the addition of the black currant anthocyanin to general foods in a large amount.

As described in Example 4, it is confirmed that black currant anthocyanin has effects on improving adaptation to darkness. As shown in Table 8, at the point where 30 min elapsed from the initiation of adaptation to darkness, from an average of 11 subjects, the indicator was recognized up to $1.39 \times 10^{-5}$ lux in the group where the black currant anthocyanin was not ingested. On the contrary, the indicator was recognized up to $1.05 \times 10^{-5}$ lux in the group where the black currant anthocyanin was ingested. Likewise, blueberry anthocyanin and black chokeberry anthocyanin show some improving effects although not as much as black currant anthocyanin. According to the present process, the subject has to specify the direction of the Landolt ring, in other words, visual acuity in darkness is measured by this process. Therefore, it could be said that the visual acuity in darkness was improved. As shown in FIG. 2, the effect on improving adaptation to darkness does not affect cones, however, improves only the threshold of adaptation to darkness by the rods. This indicates that the effect on improving adaptation to darkness affects the retinal rods.

Differences among these effects are shown in Table 1. The black currant anthocyanin with the highest potency had the highest delphinidin content of 67.0% by weight. The blueberry anthocyanin with the second highest potency had a delphinidin content of 35.1% by weight. The black chokeberry anthocyanin with the least potency had a delphinidin content of 0% by weight. This indicates that the effect on improving the adaptation to darkness is proportionally related to the delphinidin content. Among anthocyanins, the delphinidin particularly has effects on improving the adaptation to darkness.

The present inventors found that the ingestion of foods containing the black currant anthocyanin led to an improvement in visual functions in refraction value and adaptation to darkness, moreover, an improvement in myopia, lowered visual acuity, asthenopia, visual acuity in darkness, retinal function and the like. The present inventors consider that black currant anthocyanin mainly affects the retina and ciliary muscle. The retina is one of the most important optic organs. The retina cannot be subjected to transplant unlike the cornea, etc. Unlike the crystalline lens, the retina cannot be replaced with, for example, an artificial glass lens. Retinal diseases are closely related to various diseases. Improvement in retinal function is expected to be effective in, in addition to the improvement in adaptation to darkness and visual acuity in darkness, improvement in kinetic eyesight, and the prevention of or recovery from various retinal diseases, such as ocular floater, retinal detachment, and retinal macular degeneration.

The retina is equivalent to a film in a camera. Better sensitivity thereof provides very significant subjective symptoms.

The ciliary muscle is equivalent to a focusing mechanism in a camera and the crystalline lens is equivalent to a lens in a camera. Recovery of function of the crystalline lens could prevent dysfunctions, such as hyperopia, presbyopia, astigmatism, and diseases such as cataract or glaucoma, in addition to asthenopia, eyestrain, lowered visual acuity, pseudomyopia, and myopia.

Visual function comprises a plurality of functions which are intricately related to one another. Amelioration of the retina and the refracting power of the crystalline lens could result in the recovery from general visual dysfunctions, for example, afflux, blurred visual function, dazzling, dry eyes, increased discharge from the eyes, and dark areas around or under the eyes.

Anthocyanin is found to have antioxidation activity, and is presumably effective in treatment or prevention of cataract which is presumably caused by peroxides.

The effect on improving blood fluidity according to the present invention is not intended to improve blood fluidity or to lower blood pressure by relaxing vasoconstriction and dilating peripheral vessels unlike foods derived from *Physalis angulata* L. for improving the levels of blood pressure and blood sugar according to Japanese Patent Laid-Open No. 143324/1986. That is, according to the present invention, diseases such as cerebral hemorrhage and coronary heart disease are prevented by affecting erythrocytes, leukocytes, and platelets as such in the blood to improve the fluidity of the blood itself, thereby lowering blood pressure rather than by vasoconstriction.

Likewise, regarding the effects of a saffron extract on improving the peripheral blood fluidity described in Japanese Patent Laid-Open No. 287576/1998, effects and mechanisms thereof are not clearly described. Only the resistivity of peripheral vessels is lowered, and thus, it differs from the effect on improving blood fluidity according to the present invention.

Anthocyanin and anthocyanidin derived from crown of thorns according to Japanese Patent Laid-Open No. 77328/1987 are measured for their effects and mechanisms as a circulation-improving agent as follows. The left coronary artery of a rabbit is removed to measure its tension, thereby measuring the effects on vessels per se. On the contrary, according to the present invention, blood fluidity is improved by directly influencing the blood component. This indicates that the present invention is completely different from the prior art.

As described in detail in Example 12, the ingestion of juice containing 78.4 mg of the black currant anthocyanin significantly improves blood fluidity 4 hours after ingestion.

The effects on lowering blood pressure according to the present invention function in both cases, i.e., the vasoconstrictive phase (maximal blood pressure) and the vasodilative phase (minimal blood pressure). As described in detail in Example 12, the level of blood pressure is lowered by 5 to 8 mmHg for the maximal blood pressure and 2 to 13 mmHg for the minimal blood pressure. One ingestion realized this phenomenon, and thus, continuous ingestion could further lower blood pressure.

As described above, the present inventors produced, for the first time, compositions containing a large quantity of black currant anthocyanin and incorporated them into general foods to which were conventionally unable to add. As a result, the present inventors found that foods and drinks containing black currant anthocyanin had several effects for improving visual functions, effects on improving blood fluidity, and effects on lowering blood pressure as described above. Thus, they succeeded in imparting novel functions to foods and drinks.

As forms of foods incorporating the compositions containing a large quantity of black currant anthocyanin according to the present invention, foods can be any type of form in addition to those described in the examples. Forms of foods include a wide variety of types, for example; chocolates, jams and marmalades, candies, tablets, gummy confections, biscuits, crackers, cookies, pies, rice crackers and sliced and dried rice cake, juice, yogurt, dairy beverages, gelatinous beverages, desserts, such as custard puddings and jellies, fruit sauce, tea, coffee, black tea, and herb tea, fish-paste products, milk and dairy products, hams and sausages, bean pastes, soy sauce, sauce and ketchup, curries and stews, liquors, refreshing beverages, ice creams and ice cream-like products, syrups, bread, dumplings, rice cakes, bean curd, vinegar, foods boiled down in soy, pickles, foods of delicate flavor, bean jams, soft adzuki-bean jellies, flour pastes, precooked Chinese noodles, retort foods, canned foods and bottled foods, nutrition-enriched foods, and dietary supplements. An effective amount of black currant anthocyanin incorporated is at least 10 mg of anthocyanidin, about 16 mg of anthocyanin as the minimum intake necessary to realize the potency in one ingestion. However, the intake is not limited to this, and ingestion thereof in a larger amount is preferred. When separate ingestion several times a day is contemplated, the amount can be divided according to the number of times ingested. Continuous ingestion for several days provides clearer effects. Regarding the effects of improving visual function, foods may be ingested on any occasion, for example, when asthenopia is sensed, when dysfunction of eyes is sensed, and when an improvement in eye functions is contemplated. Ingestion can be made at any occasion, for example: before or in the intervals in the operation of automobiles, trains, aircrafts and the like; before or while watching televisual function, videos and the like; before, while, or after playing video games or operating personal computers; before, while, or after reading; when the eyes are in a poor condition for lack of sleep; when sunlight is dazzling; when eye fatigue is sensed; when makeup cannot be well applied; and before or in the intervals of exercise.

Regarding the effects on improving blood fluidity and lowering blood pressure, ingestion may be made at any occasion in our lives. For example, effects can be more obvious by ingesting when we have, for example, a bruise, a chap, a chilblain, a cold constitution, shoulder stiffness, numbness in hands and feet, hemorrhoids, blotch, and general malaise.

This specification includes the content described in the specifications and/or the drawings of Japanese Patent Application Nos. 188988/1999 and 321978/1999 as the basis for the priority of the present application.

The present invention will be described in more detail with reference to the following examples, though the technical scope of the present invention will not be limited to these examples only.

Example 1

Black Currant Anthocyanin-Containing Compositions for Food and a Process of Producing the Same A commercially available black currant juice concentrate (BX. 65.1, 6.6 kg) was diluted with 34.2 l of water to prepare 40.8 kg of diluted fruit juice of BX 10.6. The diluted fruit juice had a pH value of 2.6 and a black currant anthocyanin content of 0.7% by weight on the basis of solid matters. The monosaccharide content was about 40% and the organic acid content was 25%.

The diluted fruit juice was subjected to concentration using an equipment NTR-7410 provided with 1.8 m$^2$ of membrane area (Nitto Denko Co., Ltd.). This membrane is a negatively charged reverse osmosis membrane with the NaCl retention of about 10% and the average fractionated molecular weight of 2,000 to 3,000. Concentration was initiated at an inlet pressure of 15.0 kgf/cm$^2$ and an outlet pressure of 14.4 kgf/cm$^2$. At the initiation of concentration, the permeation rate was 888 ml/min and permeability was very good. Thus, the concentration was continued for 300 min by adding 20 lit of water to the concentration side as 20 l discharged. After the final addition of water, concentration was carried out until the concentrate stopped circulation. After the completion of concentration, the liquid remaining in the equipment was washed with a few liters of water and incorporated into the concentrate. The amount of liquid permeated was 190 liters in total.

The concentrate was 24 liters in total and in a general liquid state. The concentration of the concentrate on the basis of solid matters was lowered to Bx. 1.1 because a large quantity of washing water flowed thereinto. As a result of the HPLC analysis on the concentrate, the black currant anthocyanin content was 6.4% by weight on the basis of solid matters. That is, the concentration factor was about 5.6 times on the basis of solid matters. Monosaccharide was not detected at all, but the concentrate contained organic acid in an amount of about 3%. This was concentrated to about Bx. 65 using a rotary evaporator to use the concentrate in the following examples.

The black currant anthocyanin in the concentrate was composed of 50.4% by weight of delphinidin-3-o-rutinoside (3.2% by weight on the basis of solid matters), 10.8% by weight of delphinidin-3-o-glucoside (0.7% by weight on the basis of solid matters), 35.4% by weight of cyanidin-3-o-rutinoside (2.3% by weight on the basis of solid matters), and 3.4% by weight of cyanidin-3-o-glucoside (0.22% by weight on the basis of solid matters). Specifically, the content of the delphinidin glycoside was 61.2% by weight (3.9% by weight on the basis of solid matters).

This process for concentrating the black currant anthocyanin was repeated several times to provide a large quantity of samples. The samples were used in the following pulverizing step. The concentrate (Bx. 1.1) was further concentrated to Bx. 5.0 using a rotary evaporator. A solution of 10 g of maltodextrin in 800 ml of concentrate (Bx 5.0) was spray dried using a disc spray dryer. Since a portion adhered to the wall of the can and was not able to be collected, the powder obtained was 42.5 g. The black currant anthocyanin content was 5.1% by weight. As a result of the HPLC analysis, the composition of black currant anthocyanin had not changed, i.e., 50.4% by weight of delphinidin-3-o-rutinoside (2.6% by weight on the basis of solid matters), 10.8% by weight of delphinidin-3-o-glucoside (0.55% by weight on the basis of solid matters), 35.4% by weight of cyanidin-3-o-rutinoside (1.8% by weight on the basis of solid matters), and 3.4% by weight of cyanidin-3-o-glucoside (0.17% by weight on the basis of solid matters). More specifically, the content of the delphinidin glycoside was unchanged and 61.2% by weight (3.1% by weight on the basis of solid matters).

The same experiment was carried out using different black currant juice as a starting material. The results thereof are summarized in Table 3. All the test groups showed good results of an increase by about 8 to 15 times as an anthocyanin content. After concentration, organic acid and monosaccharide content significantly decreased, and thus, good properties as food materials were realized.

Example 2

Black Currant Anthocyanin-Containing Compositions for Food and a Process of Producing the Same Compositions containing a large quantity of anthocyanin (anthocyanin content of 6.4% by weight) described in Example 1 (Experiment 1 in Table 3) were used to further examine an improvement in purity by separation with chromatography.

TABLE 3

Change in ingredients in various starting fruit juice by purification

| Experiment | Anthocyanin content | Organic acid content | Monosaccharide content |
|---|---|---|---|
| Before purification (starting materials) | | | |
| 1 | 0.7 wt % | 25 wt % | 40 wt % |
| 2 | 0.4 wt % | 20 wt % | 45 wt % |
| 3 | 0.3 wt % | 25 wt % | 45 wt % |
| 4 | 0.15 wt % | 20 wt % | 45 wt % |
| After purification (concentrate, composition with high content) | | | |
| 1 | 6.4 wt % | 3 wt % | 0 wt % |
| 2 | 4.6 wt % | 3 wt % | 0 wt % |
| 3 | 3.0 wt % | 4 wt % | 0 wt % |
| 4 | 1.2 wt % | 5 wt % | 0 wt % |

The composition was passed through into a 300 ml column filled with an ion-exchange resin, Amberlite 200C (Rohm and Haas Company) to adsorb the anthocyanin component thereon. Thereafter, 1.5 l of distilled water was passed therethrough to remove an excess components. A solution (500 ml) prepared by mixing 50 parts 1% by weight of aqueous hydrochloric acid solution with 50 parts ethanol, and this solution was passed through the column to elute the anthocyanin component. The 50% ethanol fraction was concentrated by a rotary evaporator and re-dissolved in water. The re-dissolved solution was 20 ml, Bx. 15, and 3 g on the basis of solid matters. Result of HPLC analysis showed that the anthocyanin content was 25.0% by weight on the basis of solid matters. The composition of black currant anthocyanin in the concentrate had not particularly changed, i.e., 50.5% by weight of delphinidin-3-o-rutinoside (12.6% by weight on the basis of solid matters), 11.0% by weight of delphinidin-3-o-glucoside (2.75% by weight on the basis of solid matters), 34.5% by weight of cyanidin-3-o-rutinoside (8.63% by weight on the basis of solid matters), and 4.0% by weight of cyanidin-3-o-glucoside (0.73% by weight on the basis of solid matters). More specifically, the content of the delphinidin glycoside was 61.5% by weight (15.4% by weight on the basis of solid matters).

This re-dissolved solution was subjected to freezing, then freeze-drying, and pulverization. The anthocyanin content was 25% by weight on the basis of solid matters. The same procedure was repeated to prepare powders, and the powders thus obtained were used in Example 10.

Example 3

Functional Drinks Effecting Recovery from Asthenopia Caused by Computer Operation Load Ten healthy adult males and females (ages 23 to 34) without hypermetropia, presbyopia, astigmatism, or excessive myopia were subjected to a test. Subjects were divided into test groups of a black currant group, a blueberry group, and a black chokeberry group, and a control group without ingestion. A comparison test was carried out among groups by a cross over double blind experiment. In order to avoid variations caused by day, each group was randomly arranged to perform the ingestion test.

As test materials, three types of juices (200 g per bottle) were prepared using the black currant anthocyanin concentrate (black currant anthocyanin content of 6.4% by weight on the basis of solid matters) according to Example 1, a commercially available blueberry juice concentrate, and a black chokeberry juice concentrate in accordance with formulations shown in Table 7. Since the compositions were formulated so as to incorporate 40 mg of anthocyanidin (an aglycon portion of the anthocyanin) in each juice, 78.4 mg of black currant anthocyanin, 62.1 mg of black chokeberry anthocyanin, and 62.3 mg of blueberry anthocyanin were incorporated, as an amount of anthocyanin.

Because a double blind experiment was adopted, the test was carried out with the subjects and the testers unaware of the contents.

Measurement was carried out on subjects for about 15 min before ingesting test materials, and the subjects then ingested the test materials. The operation load was applied for a total of 2 hr, i.e., from 2 hr after ingestion until 4 hr after ingestion. Immediately after completion of the load, measurement was carried out. The operation load was such that a simple addition test was performed on the computer in accordance with Kraepelin's test for 2 hr without recess. The time course is shown as follows with the initiation of measurement indicated as 0:00.

| Measurement before ingestion | Ingestion | Initiation of load | Completion of load | Measurement |
|---|---|---|---|---|
| 0:00 | 0:15 | 2:15 | 4:15 | 4:30 |

The measurement was carried out using an Acomodo Auto Refractometer (Nidek Co., Ltd.) to measure and compare the refraction value at the site of relaxation of accommodation in the dominant eye before ingestion of test materials and after the operation load was applied. Prior to that, the load test and the measurement were also carried out without ingestion.

At the time of each measurement, subjective measurement of the level of fatigue by VAS was simultaneously carried out.

Computer operation on the day of testing and ingestion of caffeine, anthocyanin, and nicotine was forbidden from the morning of the testing day.

The average of differences before and after ingestion and application of the load are shown in Table 4, and results of paired-t test are shown in Table 5. As is apparent from the group without ingestion shown in Table 4, the refraction value is lowered by 0.5 D after the load. Myopia or pseudomyopia caused by asthenopia develops. Compared to the group without ingestion, every group with ingestion shows improvement in values, however; only the group which ingested black currant shows a statistically significant improving effect with a significance level of $p<0.05$. The reason for the increased standard deviation is that the original refraction value of an individual subject differs from one another.

TABLE 4

Differences before and after ingestion and load in refraction values of dominant eye in each ingestion group (positive value indicating worsened, negative value indicating improvement)

| Ingestion group | Difference before and after ingestion and load |
|---|---|
| Black currant anthocyanin | −0.470 ± 0.333 |
| Blueberry anthocyanin | 0.064 ± 0.269 |
| Black chokeberry anthocyanin | −0.097 ± 0.381 |
| Without ingestion | 0.541 ± 1.177 |

TABLE 5

Test results on differences among each ingestion group

| Groups to be compared | | p value |
|---|---|---|
| Black currant anthocyanin | Without ingestion | 0.022* |
| Blueberry anthocyanin | Without ingestion | 0.236 |
| Black chokeberry anthocyanin | Without ingestion | 0.171 |

*represents p < 0.05 and significant.

Table 6 shows the test group in which each subject sensed the best effect in alleviating asthenopia. The group, which ingested black currant anthocyanin, showed the best effect, i.e., 5 subjects out of 10. 3 subjects found the blueberry anthocyanin most effective, one subject the black chokeberry anthocyanin, and one subject without ingestion. Also in respect of subjective symptoms, black currant anthocyanin showed the best effect in improving asthenopia.

TABLE 6

Test plot with the best effect in improving fatigue by VAS

| Subject No. | Group with the best effect in improving fatigue |
|---|---|
| 1 | Blueberry anthocyanin |
| 2 | Blueberry anthocyanin |
| 3 | Black currant anthocyanin |
| 4 | Black currant anthocyanin |
| 5 | Without ingestion |
| 6 | Blueberry anthocyanin |
| 7 | Black chokeberry anthocyanin |
| 8 | Black currant anthocyanin |
| 9 | Black currant anthocyanin |
| 10 | Black currant anthocyanin |

Example 4

Functional Drinks Having Effects on Recovering Adaptation to Darkness

Eleven adult males and females (ages 23 to 50) free from eye disease were subjected to the test. Subjects were divided into the test groups of a black currant group, a blueberry group, and a black chokeberry group, and a control group without ingestion. A comparison test was carried out among groups by a cross over double blind experiment. In order to avoid variations caused by day, each group was randomly arranged to perform an ingestion test.

As test materials, three types of juices (200 g per bottle) were provided in the same manner as Example 3 in accordance with formulations shown in Table 7. As with Example 3, since the composition was formulated so as to incorporate 40 mg of anthocyanidin in each juice, 78.4 mg of black currant anthocyanin, 62.1 mg of black chokeberry anthocyanin, and 62.3 mg of blueberry anthocyanin were incorporated, as an amount of anthocyanin.

TABLE 7

Formulation of juice used in Examples 3 and 4

| Black currant anthocyanin juice | |
|---|---|
| Black currant anthocyanin concentrate according to Example 1 (Bx 65, 6.4% by weight of anthocyanin) | 2.3 wt % |
| Granulated sugar | 11.3 wt % |
| Sodium citrate | 0.4 wt % |
| Spice | 0.1 wt % |
| Water | 85.9 wt % |

TABLE 7-continued

Formulation of juice used in Examples 3 and 4

| Black chokeberry anthocyanin juice | |
|---|---|
| Black chokeberry juice (Ybbataler, Bx 65, 0.94% by weight of anthocyanin, 0.61% by weight of anthocyanidin) | 5.1 wt % |
| Granulated sugar | 13.5 wt % |
| Sodium citrate | 0.4 wt % |
| Citric acid | 1.3 wt % |
| Spice | 0.1 wt % |
| Water | 79.6 wt % |
| Blueberry anthocyanin juice | |
| Blueberry juice (Ybbataler, Bx 65, 1.43% by weight of anthocyanin, 0.94% by weight of anthocyanidin) | 3.3 wt % |
| Granulated sugar | 16.0 wt % |
| Sodium citrate | 0.4 wt % |
| Spice | 0.1 wt % |
| Water | 80.2 wt % |

Measurement was carried out on subjects for about 15 min before ingesting the test materials. Then, the test materials were ingested. 2 hr after ingestion, measurement was immediately carried out.

Measurement was carried out using a Goldmann Weekers adaptometer (Haag Streit AG) to measure partial adaptation to darkness.

At first, subjects were adapted to indoor light for 5 to 10 min. Next, the test chamber was turned into a complete darkroom, and adaptation to darkness was performed for 2 min prior to the test. Subsequently, light adaptation was performed for 10 min in a dome. Thereafter, the measurement was initiated. The measurement was carried out as follows. A target which is a Landolt ring was set for three directions of longitudinal, lateral, and diagonal directions with lowered luminance, so the subject cannot see the indicator. The luminance was gradually increased until the subject could perceive the direction of the target. The subject was then to specify the direction of the target. When the subject's perception was correct, a dot was plotted. This dot was determined as the threshold of the Dark adaptation threshold. The measurement was continued until 10 min after the initiation of the measurement at which the Kohlrausch point appeared. For 10 to 30 min after initiation, the measurement was carried out every 1 to 3 min. The measurement was terminated 30 min after initiation.

On the day of the test, computer operations and the ingestion of caffeine, anthocyanin, and nicotine was forbidden from the morning of the testing day.

Table 8 shows the results of the average and the standard deviation of the dark adaptation threshold at 30 min after the initiation of adaptation to darkness where adaptation to darkness was almost complete. Differences in standard deviation are large because the threshold of adaptation to darkness, inherent to an individual subject, greatly differs from one subject to another.

TABLE 8

Threshold of the adaptation to darkness 2 hr after ingestion in each ingestion group (30 min after the initiation of adaptation to darkness) (the smaller the value, the better)

| Ingestion group | Threshold of adaptation to darkness 2 hr after ingestion, lux |
|---|---|
| Black currant anthocyanin | $1.05 \times 10^{-5} \pm 5.51 \times 10^{-6}$ |
| Blueberry anthocyanin | $1.11 \times 10^{-5} \pm 3.67 \times 10^{-6}$ |

TABLE 8-continued

Threshold of the adaptation to darkness 2 hr after ingestion in each
ingestion group (30 min after the initiation of adaptation to darkness)
(the smaller the value, the better)

| Ingestion group | Threshold of adaptation to darkness 2 hr after ingestion, lux |
|---|---|
| Black chokeberry anthocyanin | $1.31 \times 10^{-5} \pm 5.70 \times 10^{-6}$ |
| Without ingestion | $1.39 \times 10^{-5} \pm 4.85 \times 10^{-6}$ |

As is apparent from the table, compared to the group without ingestion, in each other case with ingestion (of one of) the three types of anthocyanins there is a lowered average of the threshold of the Dark adaptation threshold, i.e., show the effect of the anthocyanin. The most effective anthocyanin was that of black currant, and subsequently, blueberry and black chokeberry, in that order. In addition, as shown in FIG. 2, none of the anthocyanins had an effect before the Kohlrausch point, but an improving effect was seen after that point. This indicates that anthocyanin affects only retinal rods without affecting retinal cones.

Example 5

Chocolate Having a Visual Function Improvement Effect

Chocolate containing a large quantity of black currant anthocyanin having cream in its center (50 g per bar) was produced. The chocolate was 40% by weight of center cream and 60% by weight of chocolate. Cream in the center comprised the powder containing a large quantity of black currant anthocyanin (black currant anthocyanin content of 5.1% by weight) according to Example 1 as described below. The chocolate was very good in quality maintaining its flavor derived from the black currant.

| | |
|---|---|
| Sugar | 20% by weight |
| Fat and oil | 44% by weight |
| Powdered milk | 30% by weight |
| Spice | 1% by weight |
| Powder obtained in Ex. 1 | 5% by weight |
| (black currant anthocyanin content of 5.1% by weight) | |

Instead of the juice according to Examples 3 and 4, a bar of the chocolate (50 g, 20 g as the center) was ingested to perform the tests described in Examples 3 and 4 on each subject respectively. In this test, 26 mg of anthocyanidin and 51 mg of black currant anthocyanin were calculated to be ingested.

As a result, the refraction value was improved by −0.32 D from −4.17 D to −3.85 D. The threshold of the Dark adaptation threshold in adaptation to darkness was $5.0 \times 10^{-6}$ lux. The subject had a threshold of $8.0 \times 10^{-6}$ lux without ingestion, and thus, both tests showed improving effects. With the black currant anthocyanin incorporated into chocolate, the effects of black currant anthocyanin for improving visual function can be seen.

Example 6

Tablet Candies Having Visual Function Improving Effects

Tablet candies containing a large quantity of black currant anthocyanin (tablet, 1 package consisting of 9 grains, 15 g) were produced. The tablet candies were produced by tableting powders, the powders comprising a large quantity of black currant anthocyanin according to Example 1 (black currant anthocyanin content of 5.1% by weight) as described below. The tablet candies were very good in quality maintaining flavor derived from black currant.

| | |
|---|---|
| Powdered sugar | 84.9% by weight |
| Citric acid | 3.5% by weight |
| Spice | 3.0% by weight |
| Emulsifier | 2.0% by weight |
| Powders obtained in Ex. 1 | 6.6% by weight |
| (black currant anthocyanin content of 5.1% by weight) | |

Instead of the juice according to Examples 3 and 4, two packages of the tablet candies (30 g) were ingested to perform the tests described in Examples 3 and 4 on each subject respectively. In this test, 51.4 mg of anthocyanidin and 100.98 mg of black currant anthocyanin were calculated to be ingested.

As a result, refraction value was improved by −0.41 D from −0.61 D to −0.20 D. The threshold of the Dark adaptation threshold in adaptation to darkness was $6.0 \times 10^{-6}$ lux. The subject had a threshold of $1.3 \times 10^{-5}$ lux without ingestion, and thus, improving effects were seen in both tests. With black currant anthocyanin incorporated into tablet candies, the effects of black currant anthocyanin of improving visual function can be seen.

Example 7

Chewing Gums Having Visual Function Improvement Effects

Chewing gums containing a large quantity of black currant anthocyanin (3 g per stick, 1 package consisting of 7 sticks) were produced by incorporating powders containing a large quantity of black currant anthocyanin (black currant anthocyanin content of 5.1% by weight) according to Example 1 as described below to shape gums. The chewing gums were very good in quality maintaining flavor derived from black currant.

| | |
|---|---|
| Sugar | 70.5% by weight |
| Gum base | 20.0% by weight |
| Spice | 3.0% by weight |
| Citric acid | 1.5% by weight |
| Powders obtained in Ex. 1 | 5.0% by weight |
| (black currant anthocyanin content of 5.1% by weight) | |

Instead of the juice according to Examples 3 and 4, one package of chewing gum (21 g) was ingested to perform the tests described in Examples 3 and 4 on each subject respectively. In this test, 27.3 mg of anthocyanidin and 53.6 mg of black currant anthocyanin were calculated to be ingested.

As a result, refraction value was improved by −0.20 D from −1.48 D to −1.28 D. The threshold of the Dark adaptation threshold in adaptation to darkness was $1.0 \times 10^{-5}$ lux. The subject had a threshold of $2.0 \times 10^{-5}$ lux without ingestion, and thus, improving effects were seen in both tests. With the black currant anthocyanin incorporated into chewing gum, the effects of black currant anthocyanin of improving visual function can be seen.

Example 8

Functional Drinks Having Visual Function Improving Effects

Drinks containing a large quantity of black currant anthocyanin (100 ml per bottle) were produced by incorporating the black currant anthocyanin concentrate (black currant anthocyanin content of 6.4% by weight on the basis of solid matters) according to Example 1 as described below. The drinks were very good in quality, maintaining flavor derived from black currant.

| | |
|---|---|
| Inverted sugar | 16.0% by weight |
| Citric acid | 0.7% by weight |
| Spice | 0.2% by weight |
| Concentrate obtained in Ex. 1 (black currant anthocyanin content of 6.4% by weight on the basis of solid matters) | 0.6% by weight |
| Water | 82.5% by weight |

Instead of the juice according to Examples 3 and 4, a bottle of the drink (100 g) was ingested to perform the tests described in Examples 3 and 4 on one subject respectively. In this test, 12 mg of anthocyanidin and 25 mg of black currant anthocyanin were calculated to be ingested.

As a result, the refraction value was improved by −0.12 D from −0.93 D to −0.81 D. The threshold of the Dark adaptation threshold in adaptation to darkness was $1.0 \times 10^{-5}$ lux. The subject had a threshold of $1.5 \times 10^{-5}$ lux without ingestion, and thus, improving effects were seen in both tests. With the black currant anthocyanin incorporated into drinks, the effects of black currant anthocyanin of improving visual function can be seen.

Example 9

Gelatinous Drinks Having Visual Function Improving Effects

Gelatinous drinks containing a large quantity of black currant anthocyanin (100 ml per bottle) were produced by incorporating powder containing a large quantity of black currant anthocyanin (black currant anthocyanin content of 5.1% by weight) according to Example 1 as described below. The gelatinous drinks were very good in quality maintaining flavor derived from black currant.

| | |
|---|---|
| Inverted sugar | 16.0% by weight |
| Citric acid | 0.7% by weight |
| Spice | 0.2% by weight |
| Gelling agent | 0.2% by weight |
| Powders obtained in Ex. 1 | 2.0% by weight |
| Water | 80.9% by weight |

Instead of the juice according to Examples 3 and 4, a bottle of the gelatinous drink (100 g) was ingested to perform the tests described in Examples 3 and 4 on each subject respectively. In this test, 51 mg of anthocyanidin and 102 mg of black currant anthocyanin were calculated to be ingested.

As a result, the refraction value was improved by −0.23 D from −1.40 D to −1.17 D. The threshold of the Dark adaptation threshold in adaptation to darkness was $5.5 \times 10^{-6}$ lux. The subject had a threshold of $9.0 \times 10^{-6}$ lux without ingestion, and thus, improving effects were seen in both tests. With black currant anthocyanin incorporated into gelatinous drinks, the effects of black currant anthocyanin for improving visual function can be seen.

Example 10

Hard Candies Having Visual Function Improving Effects

Hard candies containing a large quantity of black currant anthocyanin (3 g per candy, one package consisting of 5 candies) were produced. The powders containing a large quantity of black currant anthocyanin according to Example 2 were incorporated as follows.

The production process is as follows. At first, sucrose and the powder (black currant anthocyanin content of 25.0% by weight) according to Example 2 are added to water, followed by thorough mixing to prepare a solution. The solution is then boiled by heating. After the solution is boiled, a starch syrup is added thereto. The mixture is then heated to 145 to 150° C. to be boiled down. When the total amount is reduced to 100 in terms of proportion (initially 150.7) as a result of water evaporation, and then heating is stopped. An acidulant is added thereto, followed by stirring. The stirred mixture is then poured into a mold to be cooled in that state. Due to water evaporation, the composition of the hard candies is as follows. The hard candies were very good in quality, maintaining flavor derived from black currant.

| | Before boiled down (by weight) | After boiled down |
|---|---|---|
| Sucrose | 65.0 | About 65% by weight |
| Starch syrup | 42.0 | About 31.3% by weight |
| Citric acid | 0.7 | About 0.7% by weight |
| Powder obtained in Ex. 2 (black currant anthocyanin content of 25.0% by weight) | 3.0 | About 3% by weight |
| Water | 40.0 | About 0% by weight |

Instead of the juice according to Examples 3 and 4, a package of the hard candies (15 g) was ingested to perform the tests described in Examples 3 and 4 on each subject respectively. In this test, 57.4 mg of anthocyanidin and 113 mg of black currant anthocyanin were calculated to be ingested.

As a result, the refraction value was improved by −1.53 D from −5.78 D to −4.25 D. The threshold of the Dark adaptation threshold in adaptation to darkness was $1.5 \times 10^{-5}$ lux. The subject had a threshold of $1.8 \times 10^{-5}$ lux without ingestion, and thus, improving effects were seen in both tests. With black currant anthocyanin incorporated into hard candies, the effects of black currant anthocyanin of improving visual function can be seen.

Example 11

Anthocyanin-Enriched Jams Having Visual Function Improving Effects

Jams containing a large quantity of black currant anthocyanin (15 g per meal) were produced. Powders containing a large quantity of black currant anthocyanin (black currant anthocyanin content of 5.1% by weight) according to Example 1 were incorporated as described below. The starting material was boiled to a pulp in a kettle, thereby producing jams. As water evaporated, the total amount was reduced to 100 in terms of a proportion (initially 119.1). The jams were very good in quality, maintaining flavor derived from black currant.

|  | As incorporated (by weight) | As product |
| --- | --- | --- |
| Frozen black currant fruit | 40.0 | 30.9% by weight |
| Granulated sugar | 50.0 | 50.0% by weight |
| Powdered sugar | 5.5 | 5.5% by weight |
| Pectin | 0.3 | 0.3% by weight |
| Powder obtained in Ex. 1 (black currant anthocyanin content of 5.1% by weight) | 13.3 | 13.3% by weight |
| Water | 10.0 | 0.0% by weight |

Instead of the juice according to Examples 3 and 4, 15 g of the jams were ingested to perform the tests described in Examples 3 and 4 on each subject respectively. As a result of the analysis, 55 mg of anthocyanidin and 108 mg of black currant anthocyanin were calculated to be ingested.

As a result, the refraction value was improved by −0.82 D from −4.52 D to −3.70 D. The threshold of the Dark adaptation threshold in adaptation to darkness was $1.3 \times 10^{-5}$ lux. The subject had a threshold of $2.0 \times 10^{-5}$ lux without ingestion, and thus, improving effects were seen in both tests. With black currant anthocyanin incorporated in jams, the effects of black currant anthocyanin of improving visual function can be seen.

Examination 12

Functional Drinks Having Blood Fluidity Improving Effects

The black currant anthocyanin juice [prepared from the black currant anthocyanin concentrate (black currant anthocyanin content of 6.4% by weight on the basis of solid matters) according to Example 1] used in Example 3 was employed as a test material in this example. As an amount of anthocyanin, 78.4 mg of black currant anthocyanin was incorporated.

As a measurement before ingestion, five healthy adult males, free from particular disease and free from the application of drugs which may affect blood components such as an agent for hypercholesterolemia, were subjected to collection of heparin (105 μl of heparin based on 2 ml of blood).

This fresh whole blood obtained by the collection of heparin was poured into a micro channel array (width 7 μm, height 30 μm, depth 4.5 μm, and 8736 channels, Bloody 6-7, Hitachi Haramachi Electronics Co., Ltd.,) at a water column difference of 20 cm using MC-FAN (Santuri Kiko). The time necessary for 100 μl to pass through was determined. For whole blood samples exceeding 360 sec, the measurement was stopped and described as over 360 sec. The determined whole blood transit time was converted into the case where the transit time for the saline was 12 sec by using the transit time for 100 μl of saline measured immediately before according to the following formula: (blood transit time)×12 sec/(saline transit time).

Immediately before blood collection, blood pressure was measured three times using a digital automatic blood pressure gauze (HEM-705CP, Omron Corp.). The average of the maximal blood pressure (systolic phase) and the average of the minimal blood pressure (diastolic phase) were determined.

Same measurement was repeated 4 hr after ingestion as the measurement after ingestion. Results are shown below.

TABLE 9

| Transit time for 100 μl of whole blood (unit: sec) | | |
| --- | --- | --- |
| Subject No. | Before ingestion | 4 hr after ingestion |
| 1 | >600 | 80.5 |
| 2 | >600 | 45.6 |
| 3 | 42.1 | 39.7 |
| 4 | 86.7 | 41.4 |
| 5 | 42.7 | 38.4 |

TABLE 10

| Change in blood pressure between before ingestion and after ingestion (maximal/minimal, unit: mmHg) | | |
| --- | --- | --- |
| Subject No. | Before ingestion | 4 hr after ingestion |
| 1 | 132/87 | 124/80 |
| 2 | 144/95 | 137/93 |
| 3 | 132/88 | 126/81 |
| 4 | 118/83 | 113/79 |
| 5 | 109/77 | 104/64 |

As is apparent from these results, the ingestion of black currant anthocyanin improves blood fluidity, thereby lowering both the maximal blood pressure and the minimal blood pressure.

Example 13

Test on Stability of Drinks

As Experiment 1, 1.25 g of compositions containing a large quantity of anthocyanin (anthocyanin concentration of 6.4% by weight) according to Example 1 and Experiment 1, 1.385 g of citric acid (Wako Pure Chemical Industries, Ltd.), 0.462 g of citric acid $3Na.2H_2O$ (Wako Pure Chemical Industries, Ltd.), and 16 g of isomerized sugar 42 (Kato Kagaku) were dissolved in water. 1N NaOH solution was added thereto to adjust the pH value to 3.0. The total amount was brought to 100 g with the addition of water.

As Experiment 2, 0.32 g of compositions containing a large quantity of anthocyanin (anthocyanin concentration of 25.0% by weight) according to Example 2, 1.385 g of citric acid, 0.462 g of citric acid $3Na.2H_2O$, and 16 g of isomerized sugar 42 were dissolved in water. 1N NaOH solution was added thereto to adjust the pH value to 3.0. The total amount was brought to 100 g with the addition of water.

As a control, 1N NaOH solution was added based on 11.43 g of fruit juice before purification (anthocyanin concentration of 0.7% by weight) according to Example 1, Experiment 1 to adjust the pH value to 3.0. The total amount was brought to 100 g with the addition of water.

These three types of drinks were produced and stored at 37° C. for 2 weeks in a transparent container. The anthocyanin content in the drinks was then measured and indicated by the rate of persistence as shown in the following table. In each test group, the anthocyanin content at the initiation of the test is equivalent to one another.

TABLE 11

| | Anthocyanin employed | Rate of remain |
|---|---|---|
| Experiment 1 | Composition with a high content according to Ex. 1 | 20.6% |
| Experiment 2 | Composition with a high content according to Ex. 2 | 24.5% |
| Control | Black currant juice before purification | 1.0% |

As is apparent from the test, compositions containing a large quantity of anthocyanin according to Examples 1 and 2 have better stability compared to conventional black currant juice before purification.

All publications, patents, and patent applications cited in the present specification as such are incorporated herein as references.

INDUSTRIAL APPLICABILITY

Conventional black currant anthocyanin compositions have a low black currant anthocyanin content, strong acidity, and poor stability, and thus, are not suitable as additives for foods and drinks. However, the production process of the present invention provides black currant anthocyanin-containing compositions for food which have a high black currant anthocyanin content, adequate acidity, and stability, and thus can be added to foods and drinks. Further provided are functional foods and drinks incorporating the composition therein and having effects in improving visual function, effects in improving blood fluidity, and effects in lowering blood pressure.

The invention claimed is:

1. A black currant anthocyanin-containing composition suitable for human consumption, which comprises 5 to 25% by weight of black currant anthocyanin and an organic acid content of not more than 5% by weight on the basis of solid matters, and monosaccharide is not found.

2. The black currant anthocyanin-containing composition suitable for human consumption according to claim 1, wherein the black currant anthocyanin comprises delphinidin in an amount of 2.5 to 12.5% by weight on the basis of solid matters.

3. The black currant anthocyanin-containing composition suitable for human consumption according to claim 1, wherein the black currant anthocyanin comprises delphinidin-3-o-rutinoside in an amount of 2 to 10% by weight on the basis of solid matters.

4. A food or drink including the black currant anthocyanin-containing composition suitable for human consumption according to claim 1.

5. The food or drink according to claim 4, wherein the food or drink is candy, chewing gum, juice, chocolate, tablet, gelatinous food, or jam.

6. A black currant anthocyanin-containing composition suitable for human consumption according to claim 1, which contains an effective amount of the black currant anthocyanin for improving visual function selected from the group consisting of alleviating asthenopia compared to asthenopia before ingestion of the composition and improving adaptation to darkness as compared to adaptation to darkness before ingestion of the composition.

7. The food or drink according to claim 4, which contains an effective amount of the black currant anthocyanin for improving visual function selected from the group consisting of alleviating asthenopia compared to asthenopia before ingestion of the composition and improving adaptation to darkness as compared to adaptation to darkness before ingestion of the composition.

8. A black currant anthocyanin-containing composition suitable for human consumption according to claim 1, which has an effect for improving blood fluidity compared to blood fluidity before ingestion of the composition and/or an effect for lowering blood pressure compared to blood pressure before ingestion of the composition.

9. The food or drink according to claim 4, which has at least one of an effect for improving blood fluidity compared to blood fluidity before ingestion of the composition and an effect for lowering blood pressure compared to blood pressure before ingestion of the composition.

10. The black currant anthocyanin-containing composition suitable for human consumption according to claim 1, which is prepared by purifying, separating and concentrating the black currant anthocyanin in a retentate with a negatively charged reverse osmosis membrane from monosaccharides and acids contained in a black currant raw material.

11. The black currant anthocyanin-containing composition suitable for human consumption according to claim 1 further processed into a form of a member selected from the group consisting of a paste, gel and powder.

12. The black currant anthocyanin-containing composition suitable for human consumption according to claim 1, wherein the black currant anthocyanin comprises delphinidin in an amount of 2.5 to 15.7% by weight on the basis of solid matters.

13. The black currant anthocyanin-containing composition suitable for human consumption according to claim 1, wherein black currant anthocyanin comprises delphinidin-3-o-rutinoside in an amount of 2 to 13.2% by weight on the basis of solid matters.

14. A black currant anthocyanin-containing composition suitable for human consumption, which comprises:
at least one anthocyanin derived from black currant and selected from the group consisting of delphinidin-3-o-glucoside, delphinidin-3-o-rutinoside, cyanidin-3-o-glucoside and cyanidin-3-o-rutinoside, the at least one anthocyanin derived from black currant being contained in an amount from 5 to 25% by weight based on total amount of black currant solid matters contained in the composition,
an organic acid content of not more than 5% by weight based on total amount of black currant solid matters contained in the composition, and
monosaccharide is not found.

15. The black currant anthocyanin-containing composition suitable for human consumption according to claim 14, wherein the at least one anthocyanin derived from black currant anthocyanin is at least one member selected from the group consisting of delphinidin-3-o-glucoside and delphinidin-3-o-rutinoside in an amount of 2.5 to 15.7% by weight based on total amount of black currant solid matters contained in the composition.

16. The black currant anthocyanin-containing composition suitable for human consumption according to claim 14, wherein the at least one anthocyanin derived from black currant comprises delphinidin-3-o-rutinoside in an amount of 2 to 13.2% based on total amount of black currant solid matters contained in the composition.

17. The black currant anthocyanin-containing composition suitable for human consumption according to claim 1, wherein the percent by weight on the basis of solid matters equals percent by weight on the basis of black currant solid matters.

18. The black currant anthocyanin-containing composition suitable for human consumption according to claim 14, wherein the black currant anthocyanin comprises delphinidin in an amount of 2.5 to 12.5% by weight on the basis of solid matters.

19. The black currant anthocyanin-containing composition suitable for human consumption according to claim 14, wherein the black currant anthocyanin comprises delphinidin-3-o-rutinoside in an amount of 2 to 10% by weight on the basis of solid matters.

20. A food or drink including the black currant anthocyanin-containing composition suitable for human consumption according to claim 14.

21. The black currant anthocyanin-containing composition suitable for human consumption according to claim 14, which is prepared by purifying, separating and concentrating the black currant anthocyanin in a retentate with a negatively charged reverse osmosis membrane from monosaccharides and acids contained in a black currant raw material.

* * * * *